(12) United States Patent
Ammon et al.

(10) Patent No.: US 8,916,009 B2
(45) Date of Patent: Dec. 23, 2014

(54) ENDODONTIC INSTRUMENTS AND METHODS OF MANUFACTURING THEREOF

(75) Inventors: Dan Ammon, Tulsa, OK (US); Vincent Shotton, Broken Arrow, OK (US); Yong Gao, Broken Arrow, OK (US); Randall Maxwell, Broken Arrow, OK (US)

(73) Assignee: DENTSPLY International Inc., York, PA (US)

( * ) Notice: Subject to any disclaimer, the term of this patent is extended or adjusted under 35 U.S.C. 154(b) by 77 days.

(21) Appl. No.: 13/300,506

(22) Filed: Nov. 18, 2011

(65) Prior Publication Data

US 2012/0282571 A1 Nov. 8, 2012

Related U.S. Application Data

(63) Continuation-in-part of application No. 13/102,439, filed on May 6, 2011.

(51) Int. Cl.
*C22F 1/10* (2006.01)
*A61C 5/02* (2006.01)

(52) U.S. Cl.
CPC . *A61C 5/023* (2013.01); *C22F 1/10* (2013.01); *A61C 2201/007* (2013.01)
USPC .............................. 148/563; 148/564; 148/675

(58) Field of Classification Search
None
See application file for complete search history.

(56) References Cited

U.S. PATENT DOCUMENTS

| | | | | |
|---|---|---|---|---|
| 4,631,094 | A | * | 12/1986 | Simpson et al. ............... 148/563 |
| 4,889,487 | A | | 12/1989 | Lovaas |
| 5,607,435 | A | | 3/1997 | Sachdeva et al. |
| 5,697,906 | A | * | 12/1997 | Ariola et al. ............... 604/96.01 |
| 6,149,501 | A | | 11/2000 | Farzin-Nia et al. |
| 6,315,558 | B1 | | 11/2001 | Farzin-Nia et al. |
| 6,428,317 | B1 | | 8/2002 | Abel |
| 6,598,280 | B1 | * | 7/2003 | Giba et al. ...................... 29/447 |
| 6,797,083 | B2 | * | 9/2004 | Peterson ...................... 148/563 |
| 7,207,111 | B2 | | 4/2007 | Aloise et al. |
| 7,648,599 | B2 | | 1/2010 | Berendt |
| 7,713,059 | B2 | | 5/2010 | Hof et al. |
| 2004/0148011 | A1 | * | 7/2004 | Shiu et al. ..................... 623/1.13 |
| 2007/0072147 | A1 | | 3/2007 | Berendt |
| 2007/0293939 | A1 | * | 12/2007 | Shrivastava et al. ......... 623/1.16 |

FOREIGN PATENT DOCUMENTS

| | | |
|---|---|---|
| CH | 700823 B1 | 10/2010 |
| EP | 1060280 B1 | 4/2004 |
| EP | 1661528 A1 | 5/2006 |
| WO | 2009070784 A1 | 6/2009 |
| WO | 2010030668 A1 | 3/2010 |
| WO | 2011062970 A1 | 5/2011 |

OTHER PUBLICATIONS

Alapati S B et al: Micro-XRD and Tenperature-modulated DSC Investigation of Nickel-titanium Rotary Endodontic Instruments; Dental Materials, Elsevier, vol. 25, No. 10, Oct. 1, 2009 pp. 1221-1229.
Alapati S B et al: Metallurgical Characterization of a New Nickel-Titanium Wire for Rotary Endodontic Instruments; Journal of Endodontics, Lippincott, Williams & Wilkins, Philadelphia, Pa, US vol. 35, No. 11; Nov. 1, 2009 pp. 1589-1593.

* cited by examiner

*Primary Examiner* — George Wyszomierski
(74) *Attorney, Agent, or Firm* — David A. Zdurne; Douglas J. Hura; Leana Levin

(57) ABSTRACT

A method for manufacturing a nonlinear superelastic file comprising the steps of: providing a superelastic file having a shaft and a file axis; providing a fixture including a file groove being defined by one or more displacement members, the file groove configured for receiving the shaft; inserting at least a portion of the shaft into the fixture along the file groove, the portion of the shaft including a first portion of the shaft; contacting the first portion of the shaft with a first displacement member of the one or more displacement members such that the first portion of the shaft is displaced from the file axis thereby forming a first offset portion of the shaft; heating the portion of the shaft while inserted in the fixture to a temperature of at least about 300° C. for a time period of at least about 1 minute to shape-set the portion of the shaft thereby forming a shape-set nonlinear file.

46 Claims, 23 Drawing Sheets

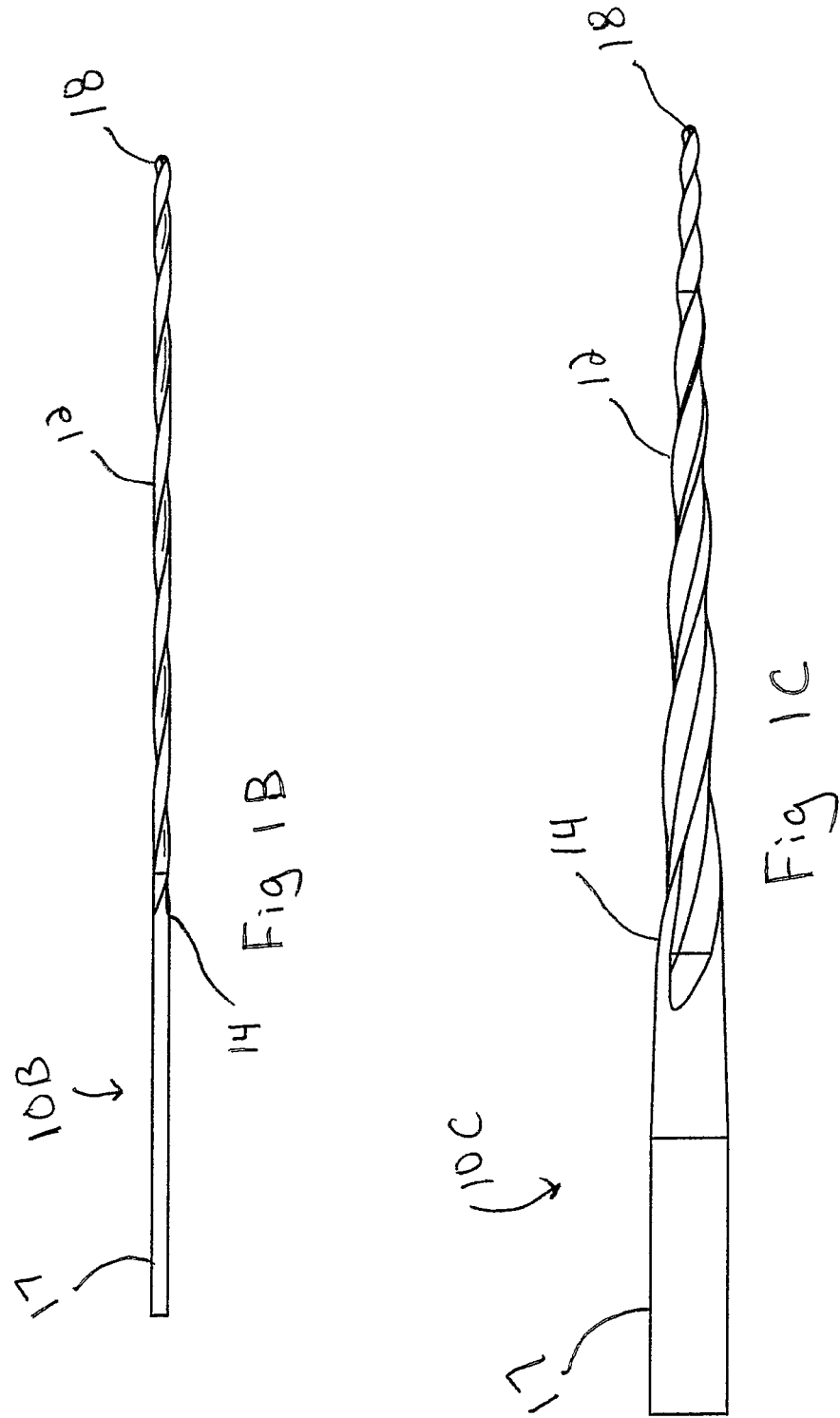

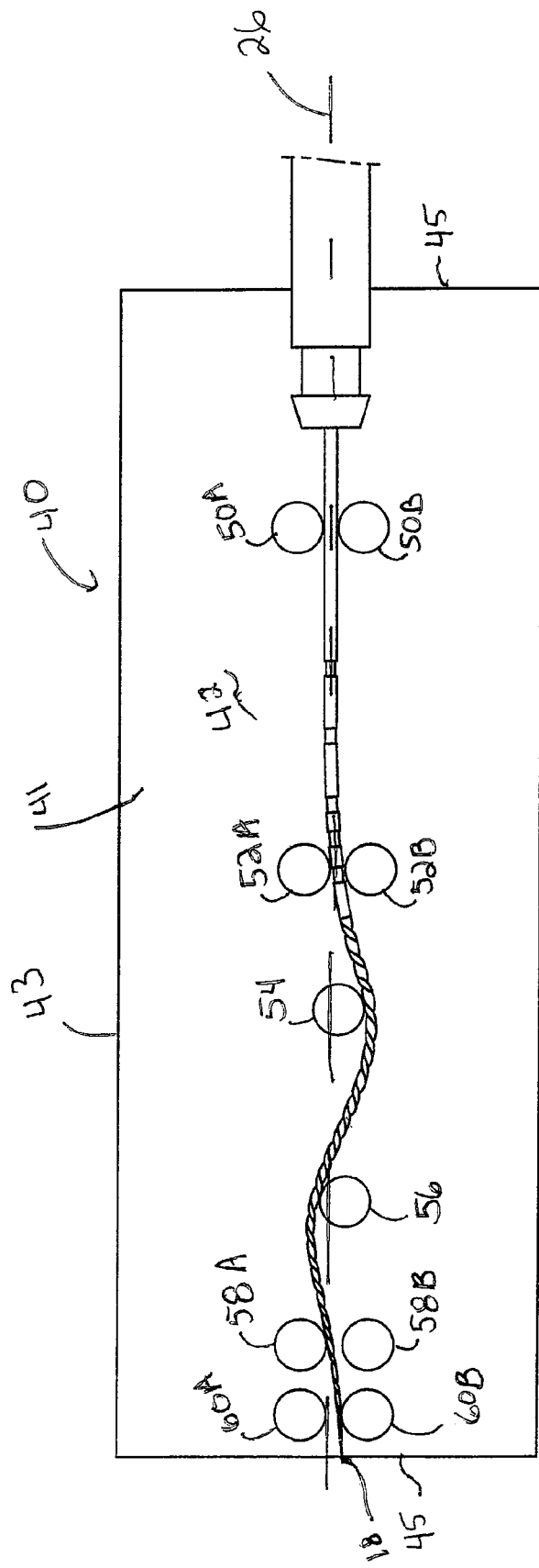
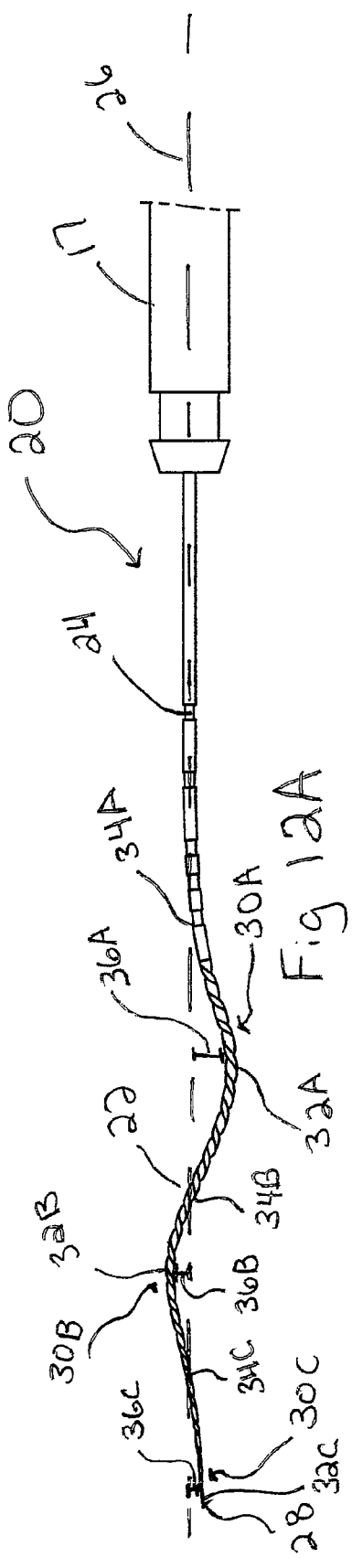
Fig 13
Fig 12A

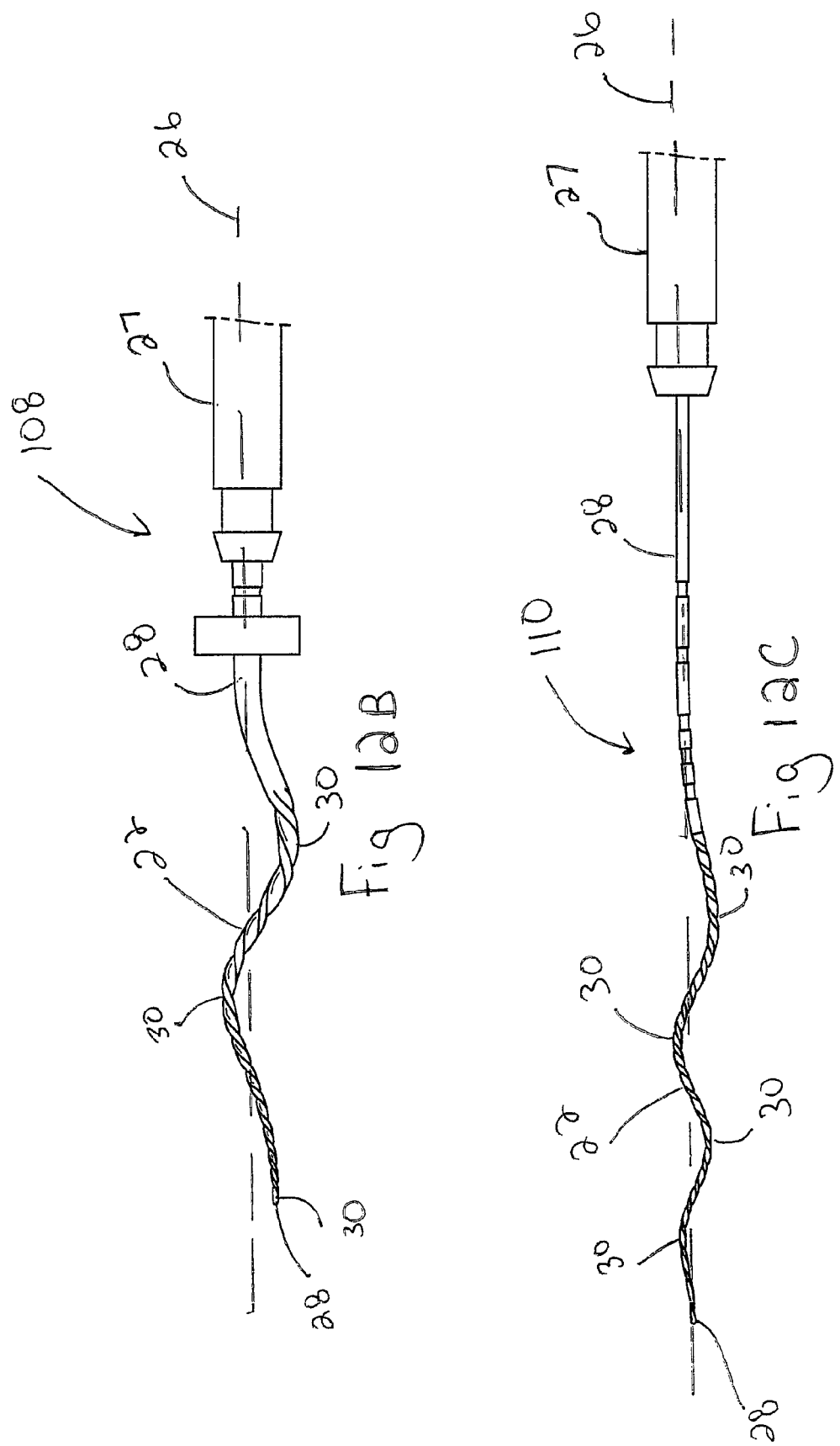

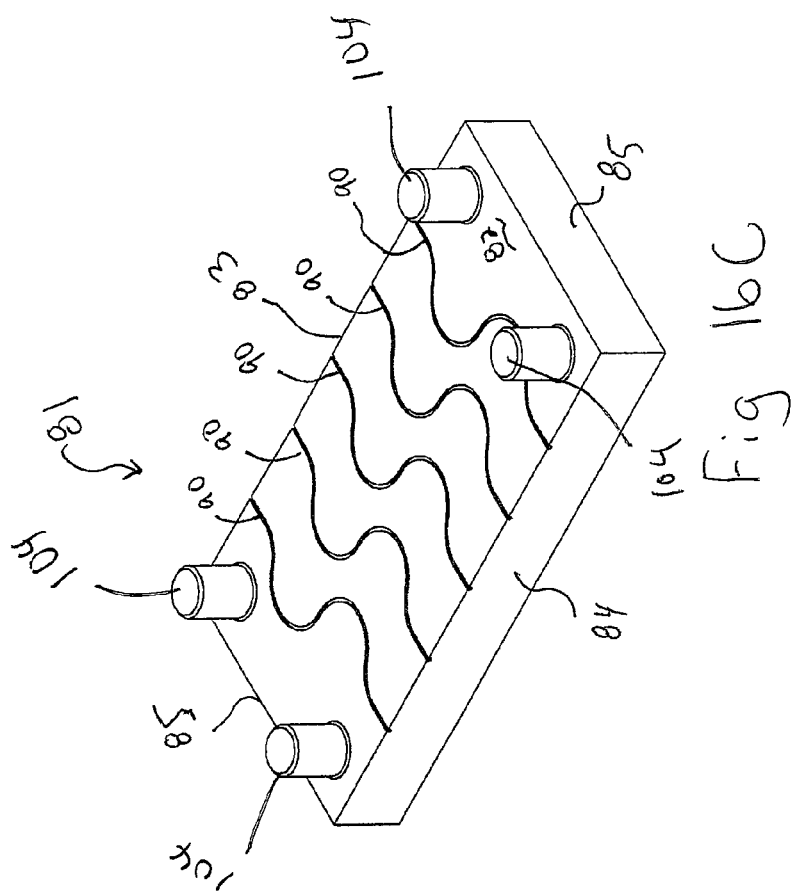
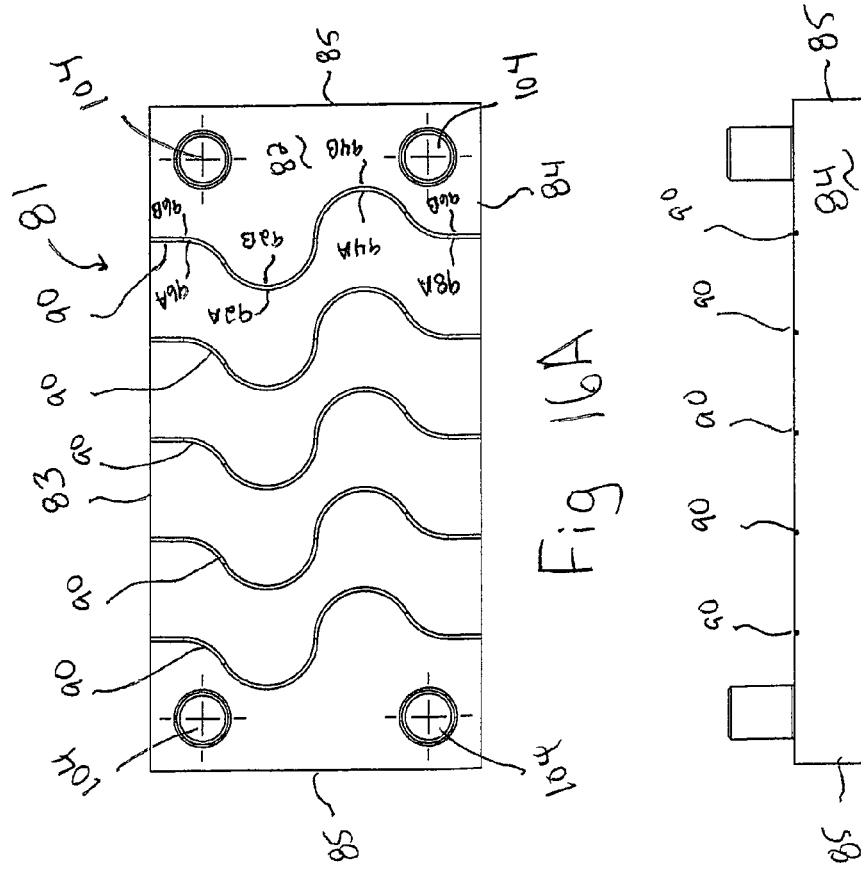

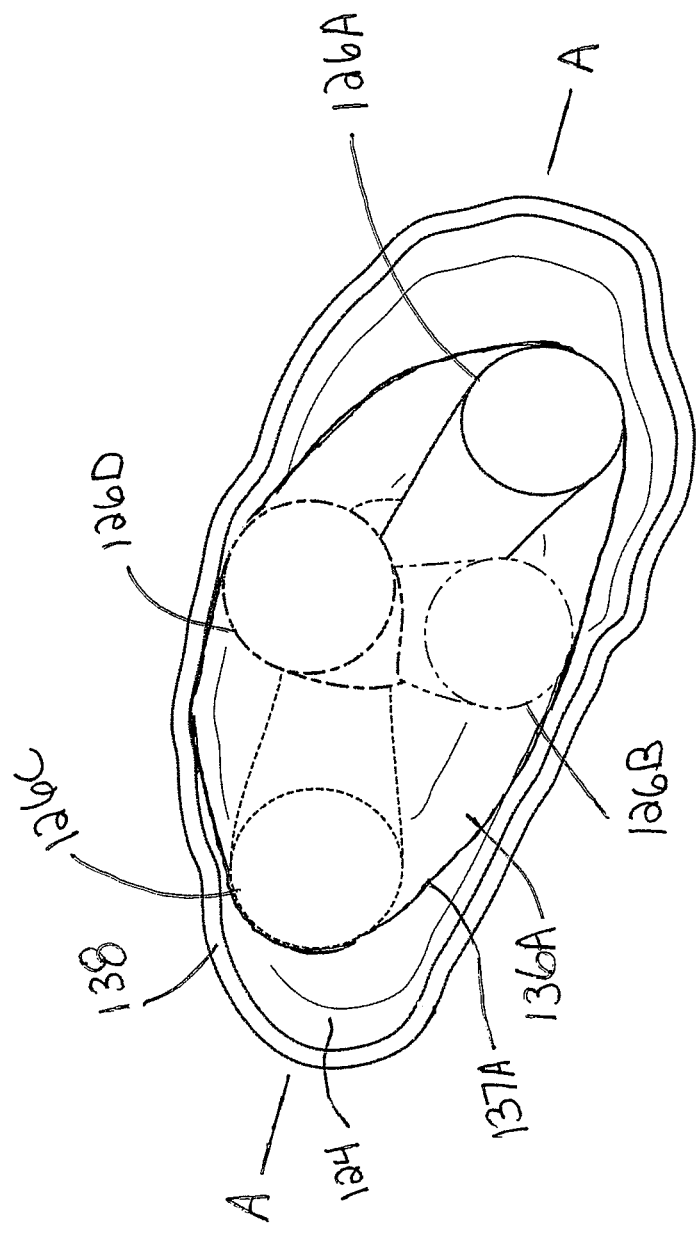

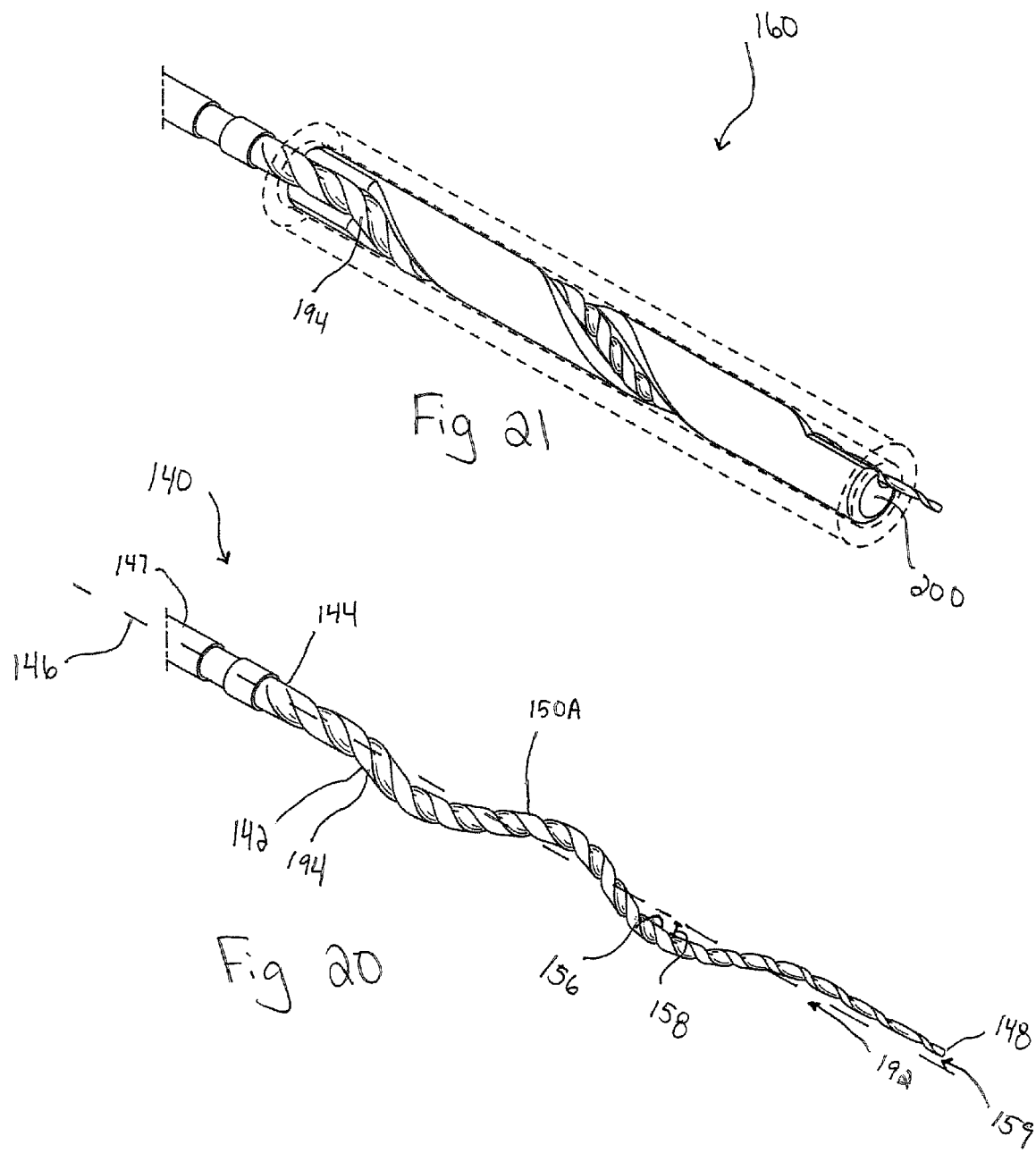

ENDODONTIC INSTRUMENTS AND METHODS OF MANUFACTURING THEREOF

FIELD OF INVENTION

The present invention is directed to a method for treating a dental instrument, and specifically to a rotary file useful for shaping and cleaning root canals.

BACKGROUND OF THE INVENTION

The endodontic instruments (including files and reamers) are used for cleaning and shaping the root canals of infected teeth. They may be in mode of either rotation or reciprocation in the canal by dentists, either manually or with the aid of dental handpieces onto which the instruments are mounted. Instruments are generally used in sequence (depending on different root canal surgery techniques) in order to achieve the desired outcome of cleaning and shaping. The endodontic instrument is subjected to substantial cyclic bending and torsional stresses as it is used in the process of cleaning and shaping a root canal. Because of the complex curvature of root canals, a variety of unwanted procedural accidents such as ledging, transportation, perforation, or instrument separation, can be encountered in the practice of endodontics.

Currently, endodontic rotary instruments made of Shape Memory Alloys (SMA) have shown better overall performance than stainless steel counterparts. However, the occurrence of unwanted procedural accidents mentioned above has not been drastically reduced. Therefore, it necessitates new endodontic instruments with improved overall properties, especially flexibility and resistance to fracture either due to cyclic fatigue and torsional overload.

U.S. Pat. No. 4,889,487 discusses an endodontic file having one or more elongated, bow-shaped bends for being used to enlarge and shape the root canal. Since not all root canals have the same geometry, a conventional tapered file typically produces a circular cross-section thereby limiting the removing the dentin and soft tissue from the canal to generally one sized canal opening corresponding to the circular-cross-section of the conventional file. This patent discusses crimping the file between to stamping member to shape the file to the desired bend radius. The problem with crimping a file is that the tool used to crimp may potentially damage the fluting of the file thus making less efficient in cutting. Another issue with crimping a file is that it inherently weakens the file in that crimped area thus making it more susceptible to breaking within the canal. U.S. Pat. No. 7,713,059 discusses an instrument for cleaning and/or shaping and/or widening a channel for a root canal. This design having an inner volume enclosed by the instrument and its outer contour may be allowed to change as a result of the forces exerted on it while working.

One possibly advantage of the present invention as compared to conventional rotary files is a method for forming a non-superelastic file. Another possibly advantage of the present invention as compared to conventional rotary files is a method for forming a nonlinear file (e.g., a non-superelastic nonlinear file) that may be able to change shape and geometry by either expanding or collapsing while shaping a root canal. Also, by shaping the rotary file with this process of using a fixture to shape set a shape memory alloy (e.g., NiTi), it may prevent the fluting from being damaged as well as maintaining the geometry throughout the process of preparing a root canal.

SUMMARY OF THE INVENTION

The present invention seeks to improve upon prior endodontic instruments by providing an improved process for manufacturing endodontic instruments. In one aspect, the present invention provides a method for manufacturing a nonlinear superelastic file comprising the steps of: providing a superelastic file having a shaft and a file axis; providing a fixture including a file groove being defined by one or more displacement members, the file groove configured for receiving the shaft; inserting at least a portion of the shaft into the fixture along the file groove, the portion of the shaft including a first portion of the shaft; contacting the first portion of the shaft with a first displacement member of the one or more displacement members such that the first portion of the shaft is displaced from the file axis thereby forming a first offset portion of the shaft; heating the portion of the shaft while inserted in the fixture to a temperature of at least about 300° C. for a time period of at least about 1 minute to shape-set the portion of the shaft thereby forming a shape-set nonlinear file In another aspect, the present invention contemplates a method for manufacturing a nonlinear superelastic file comprising the steps of: providing a superelastic linear file having a shaft and a file axis; providing a fixture including an inner member and an cover member, at least one of the inner member and the cover member having a file groove being defined by one or more displacement members, the file groove being configured for receiving the shaft and at least a portion of the file groove extending along a predetermined nonlinear file path in a spiral-like manner; inserting at least a portion of the shaft into the fixture along the file groove, the portion of the shaft including a first portion of the shaft; contacting the first portion of the shaft with a first displacement member of the one or more displacement members such that the first portion of the shaft is displaced from the file axis thereby forming a first offset portion of the shaft, the first offset portion of the shaft and the file axis defining a first plane; contacting a second portion of the portion of the shaft with a second displacement member of the one or more displacement members such that the second portion of the shaft is displaced from the file axis thereby forming a second offset portion of the shaft, the second offset portion of the shaft defines a second plane different from the first plane; and heating the portion of the shaft to a temperature of at least about 300° C. for a time period of at least about 5 minutes to shape-set the portion of the shaft thereby forming a shape-set nonlinear file.

In another aspect, the present invention contemplates a nonlinear file comprising a file axis and a shaft having a proximal end and a tip with a working portion therebetween; the shaft having at least one offset portion including a first offset portion, the first offset portion being displaced from the file axis such that the first offset portion and the file axis define a first plane.

In another aspect, the present invention contemplates a nonlinear file comprising a file axis and a shaft having a proximal end and a tip with a working portion therebetween; the shaft having at least one offset portion including a first offset portion and a second offset portion, each of the first offset portion and the second offset portion being displaced from the file axis such that the first offset portion of the shaft and the file axis define a first plane and the second offset portion defines a second plane different from the first plane.

In another aspect, the present invention contemplates a method for cleaning and shaping a root canal of a tooth, the tooth including a tooth pulp chamber and a dentin layer generally surrounding the tooth pulp chamber, the root canal having a proximal portion adjacent the tooth pulp chamber and tapering to an apex portion adjacent the tooth, the dentin/pulp interface generally defining the root canal wall, comprising the steps of: inserting into the root canal the shape-set nonlinear file including a file axis and a shaft having a proximal end and a tip with a working portion therebetween, the shaft having at least one offset portion including a first offset portion, the first offset portion being displaced from the file axis such that the first offset portion and the file axis define a first plane; rotating, reciprocating, or oscillating vertically or any combination thereof and axially advancing the nonlinear file within the root canal; contacting the first offset portion with the root canal wall such that the first offset portion collapses to minimize removal of the dentin layer thereby expanding a second offset portion to increase surface contact with the remaining pulp chamber for removal thereof.

In another aspect, the present invention contemplates a method for cleaning and shaping a root canal of a tooth, the tooth including a tooth pulp chamber and a dentin layer generally surrounding the tooth pulp chamber, the root canal having a proximal portion adjacent the tooth pulp chamber and tapering to an apex portion adjacent the tooth, the dentin/pulp interface generally defining the root canal wall, comprising the steps of: inserting into the root canal the shape-set nonlinear file including a file axis and a shaft having a proximal end and a tip with a working portion therebetween, the shaft having at least one offset portion including a first offset portion and a second offset portion, each of the first offset portion and the second offset portion being displaced from the file axis such that the first offset portion of the shaft and the file axis define a first plane and the second offset portion defines a second plane different from the first plane; rotating, reciprocating, oscillating vertically, or any combination thereof and axially advancing the nonlinear file within the root canal; contacting a first portion of the continual offset portion with the root canal wall such that the first offset portion collapses to minimize removal of the dentin layer thereby expanding a second portion of the continual offset portion to increase surface contact with the remaining pulp chamber for removal thereof.

In another aspect, the present invention contemplates a method for manufacturing a non-superelastic file comprising the steps of: providing a superelastic file having an austenite finish temperature; and heating at least a portion of the superelastic file to a temperature from about 300° C. to about 600° C. for a period of time from about 5 minutes to about 120 minutes to alter the austenite finish temperature thereby forming the non-superelastic file; wherein the altered austenite finish temperature of the non-superelastic file is from about 20° C. to about 40° C.

In yet another aspect, any of the aspects of the present invention may be further characterized by one or any combination of the following features: wherein the heating step, the portion of the shaft is heated to a temperature from about 300° C. to about 650° C. for a time period from about 1 minute to about 45 minute to shape-set the portion of the shaft thereby forming the shape-set nonlinear file; wherein the heating step, the portion of the shaft is heated to a temperature from about 350° C. to about 600° C. for a time period from about 3 minutes to about 30 minutes to shape-set the portion of the shaft thereby forming the shape-set nonlinear file; wherein the heating step, the portion of the shaft is heated to a temperature from about 450° C. to about 550° C. for a time period from about 5 minutes to about 20 minutes to shape-set the portion of the shaft thereby forming the shape-set nonlinear file; further comprising the step of cooling the portion of the shaft to form the shape-set nonlinear file and heating at least a portion of the cooled shape-set nonlinear file to a temperature from about 300° C. to about 600° C. for a period of time from about 20 minutes to about 120 minutes to alter the austenite finish temperature thereby forming a shape-set non-superelastic nonlinear file, and wherein the altered austenite finish temperature of the shape-set non-superelastic nonlinear file is from about 20° C. to about 40° C.; further comprising the step of cooling the portion of the shaft to form the shape-set nonlinear file and heating at least a portion of the cooled shape-set nonlinear file to a temperature from about 400° C. to about 500° C. for a period of time from about 40 minutes to about 70 minutes to alter the austenite finish temperature thereby forming a shape-set non-superelastic nonlinear file, and wherein the altered austenite finish temperature of the shape-set non-superelastic nonlinear file is from about 20° C. to about 40° C.; further comprising the step of contacting a second portion of the shaft with a second displacement member of the one or more displacement members such that the second portion of the shaft is displaced from the file axis thereby forming a second offset portion of the shaft, wherein the first offset portion of the shaft and the file axis define a first plane and the second offset portion defines a second plane different from the first plane; wherein the one or more displacement members further includes a second displacement member and the file groove is further defined by a pair of guiding members for receiving a guide portion of the shaft therebetween, the pair of guiding members being configured for maintaining the guide portion of the shaft from being displaced from the file axis while the first displacement member displaces the first portion of the shaft away from the file axis and the second displacement member displaces a portion of the shaft towards the file axis; wherein the first displacement member, the second displacement member, and the pair of guiding members defining the file groove form a predetermined curved nonlinear file path that orientates the portion of the shaft into a generally C-shaped profile; wherein the one or more displacement members further includes a second displacement member and a third displacement member, and the file groove is further defined by a pair of guiding members for receiving a guide portion of the shaft therebetween, the pair of guiding members being configured for maintaining the guide portion of the shaft from being displaced from the file axis while the first displacement member displaces the first portion of the shaft away from the file axis, the second displacement member displaces a second portion of the shaft away from the first displacement member and back through the file axis, and the third displacement member displaces the a third portion of the shaft from the second displacement member and towards the file axis; wherein the first displacement member, the second displacement member, the third displacement member, and the pair of guiding members that define the file groove form a predetermined curved nonlinear file path having at least two arcuate portions that orientate the portion of the shaft into a generally S-shaped profile; wherein the file groove defines a first predetermined nonlinear file path and at least one of the one or more displacement members are movable relative to the file axis so that the file groove is a variable file groove configured to define the first predetermined nonlinear file path or a second predetermined nonlinear file path that is different from the first predetermined nonlinear file path; wherein the one or more displacement members includes at least two displacement member that are movable either independently or simultaneously relative to the file axis so that the file groove is a variable file groove configured to define the first predetermined nonlinear file path or a second predetermined nonlinear file path that is different from the first predetermined nonlinear file path; wherein the file groove extends along the inner member, the cover member, or a portion of both the inner member and the cover member in the spiral-like manner; wherein the cover member at least partially covers the portion of the file groove extending in a spiral-like manner so that upon inserting the portion of the shaft into the fixture, the portion of the shaft is maintained within the file groove; wherein the inner member includes a fixture axis that is generally co-linear with the file axis such that the portion of the file groove extending in a spiral-like manner is continually displaced from the fixture axis thereby continually displacing a corresponding portion of the shaft extending therein from the file axis; wherein the shaft includes a shaft length and at least about 50% of the shaft length is continually displaced radially from the file axis; wherein the first offset portion extends between a first shaft portion and a second shaft portion defining a curve having a crest therebetween, the crest being displaced from the first shaft portion and the second shaft portion, each of the first shaft portion and the second shaft portion being generally located about the file axis so that the nonlinear file includes a generally C-shaped profile; wherein the at least one offset portion further includes a second offset portion displaced from the file axis, the first offset portion extends between a first shaft port and a second shaft portion defining a first curve having a first crest therebetween and the second offset portion extends between the second shaft portion and a third shaft portion defining a second curve having a second crest therebetween, each of the first shaft portion and the second shaft portion being generally located about the file axis so that the nonlinear file includes a generally S-shaped profile; wherein the first offset portion and the second offset portion define a continual offset portion that extends in a spiral-like manner being continually displaced radially from the file axis; wherein the shaft includes a shaft length and the continual offset portion extends in the spiral-like manner along at least about 50% of the shaft length; wherein the continual offset portion extends between a first portion of the shaft and a second portion of the shaft, the second portion of the shaft being further displaced from the file axis than the first portion of the shaft and the second portion of the shaft being located closer to the tip than the first portion of the shaft; wherein a distance between the shaft and the file axis continually increases from the first portion of the shaft to the second portion of the shaft; wherein the at least one offset portion during rotation of the nonlinear file forms a canal opening having an overall perimeter greater than the overall perimeter of a canal opening formed by a conventional linear file having a similar file taper and a similar shaft length at a same depth of the root canal during the shaping and cleaning thereof; wherein the at least one offset portion during rotation of the nonlinear file forms a canal opening having an overall perimeter greater than the overall perimeter of a canal opening formed by a conventional linear file having a similar file taper and a similar shaft length at a same depth of the root canal during the shaping and cleaning thereof; wherein the at least one offset portion during rotation of the nonlinear file forms a canal opening having an overall perimeter less than the overall perimeter of a canal opening formed by a conventional linear file having a conventional file taper and a similar shaft length at a same depth of the root canal during the shaping and cleaning thereof; wherein the at least one offset portion includes a first offset portion and a second offset portion, the first offset portion during rotation of the nonlinear file forms a canal opening having an overall perimeter greater than the overall perimeter of a canal opening formed by a conventional linear file having a similar file taper and a similar shaft length at a same depth of the root canal during the shaping and cleaning thereof, and second offset portion during rotation of the nonlinear file forms a canal opening having an overall perimeter less than the overall perimeter of a canal opening formed by a conventional linear file having a conventional file taper and a similar shaft length at a same depth of the root canal during the shaping and cleaning thereof; wherein heating the step, the temperature is from about 300° C. to about 600° C. for a period of time from about 5 minutes to about 120 minutes to alter the austenite finish temperature thereby forming the non-superelastic file, and wherein the altered austenite finish temperature of the non-superelastic file is from about 20° C. to about 38° C.; wherein the heating step, the temperature is from about 400° C. to about 500° C. for a period of time from about 40 minutes to about 70 minutes to alter the austenite finish temperature thereby forming the non-superelastic file, and wherein the altered austenite finish temperature of the non-superelastic file is from about 20° C. to about 35° C.; further comprising the step of cooling the portion of the non-superelastic file and heating at least a portion of the cooled non-superelastic file to a temperature from about 300° C. to about 650° C. for a time period from about 1 minute to about 45 minute to shape-set the portion of the shaft thereby forming a shape-set non-superelastic nonlinear file; further comprising the step of cooling the portion of the non-superelastic file and heating at least a portion of the cooled non-superelastic file to a temperature from about 350° C. to about 600° C. for a time period from about 3 minutes to about 30 minutes to shape-set the portion of the shaft thereby forming a shape-set non-superelastic nonlinear file; wherein the non-superelastic wire includes a shape memory alloy; wherein the shape memory alloy includes nickel and titanium; wherein the shape memory alloy is a nickel-titanium based binary alloy; wherein the shape memory alloy is a nickel-titanium based ternary alloy; wherein the nickel-titanium based ternary alloy of the formula Ni—Ti—X wherein X is Co, Cr, Fe, or Nb; wherein the shape memory alloy includes a copper based alloy, an iron based alloy or a combination of both; wherein the shape memory alloy is the copper based alloy includes CuZnAl or CuAlNi; wherein the shape memory alloy is the iron based alloy includes FeNiAl, FeNiCo, FeMn-SiCrNi or FeNiCoAlTaB; further comprising the step of providing a handle and attaching the handle to a portion of the nonlinear rotary file; wherein the handle is located distally from the flute(s), groove(s), or any combination thereof; further comprising the step of providing a handle and attaching the handle to a portion of the nonlinear hand file; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise.

BRIEF DESCRIPTION OF THE DRAWINGS

FIG. 1A-1C are elevational views of typical endodontic instruments having various degrees of file taper.

FIG. 2 is an elevational cross-sectional view of a molar human tooth showing the root system and the coronal area penetrated by a hole to expose the root canal system.

FIGS. 12A-12C show various embodiments of the present invention including shape-set nonlinear two dimensional files.

FIG. 13 shows another embodiment of the present invention including a fixture for forming the shape-set nonlinear file of FIG. 12A.

FIGS. 15A-16C show another embodiment of the present invention including a fixture for forming multiple shape-set nonlinear files.

FIG. 19B show the tooth preparation of FIG. 19A taken along the transverse cross-section A-A.

FIG. 20 shows another embodiment of the present invention including shape-set nonlinear three dimensional file.

FIGS. 21-23 show another embodiment of the present invention including a fixture for forming the shape-set nonlinear file of FIG. 20.

DETAILED DESCRIPTION OF INVENTION

Superelastic materials are typically metal alloys which return to their original shape after substantial deformation. Examples of efforts in the art towards superelastic materials are found in U.S. Pat. No. 6,149,501, which is herein incorporated by reference for all purposes.

Superelasticity may be generally defined as a complete rebound to the original position after deformation. However, in the industry, it is appreciated that less than 0.5% permanent set (after stretch to 6% elongation) would be acceptable. For example, if the file does not reverse to its original position, it may no longer be considered a superelastic Shape Memory Alloy (SMA) (e.g., it may not be considered a superelastic SMA if it does not return to a generally original position such as a generally straight position). Superelastic alloys such as nickel titanium (NiTi) or otherwise can withstand several times more strain than conventional materials, such as stainless steel, without becoming plastically deformed.

This invention relates to dental instruments in general. Specifically, this invention relates to endodontic instruments for use in root canal cleaning and shaping procedures. The present invention provides an innovation of endodontic instrument that is made of shape memory alloys (SMA) such as Nickel-Titanium (NiTi) based systems, Cu based systems Fe based systems, or any combination thereof (e.g., materials selected from a group consisting of near-equiatomic Ni—Ti, Ni—Ti—Nb alloys, Ni—Ti—Fe alloys, Ni—Ti—Cu alloys, beta-phase titanium and combinations thereof).

In a first embodiment, the present invention provides a method for forming an endodontic instrument made of shape memory alloys in a non-superelastic martensitic state. The non-superelastic file may provide more flexibility and increased fatigue resistance through an optimized microstructure while effectively shaping and cleaning root canals.

In another embodiment, the present invention includes an endodontic instrument made of a shape memory alloy shape-set in a predetermined nonlinear design, and methods for manufacturing thereof. The shape-set nonlinear superelastic file may provide increased ability to change shape and geometry by either expanding or collapsing while shaping and cleaning canals.

Figures 1A, 2:
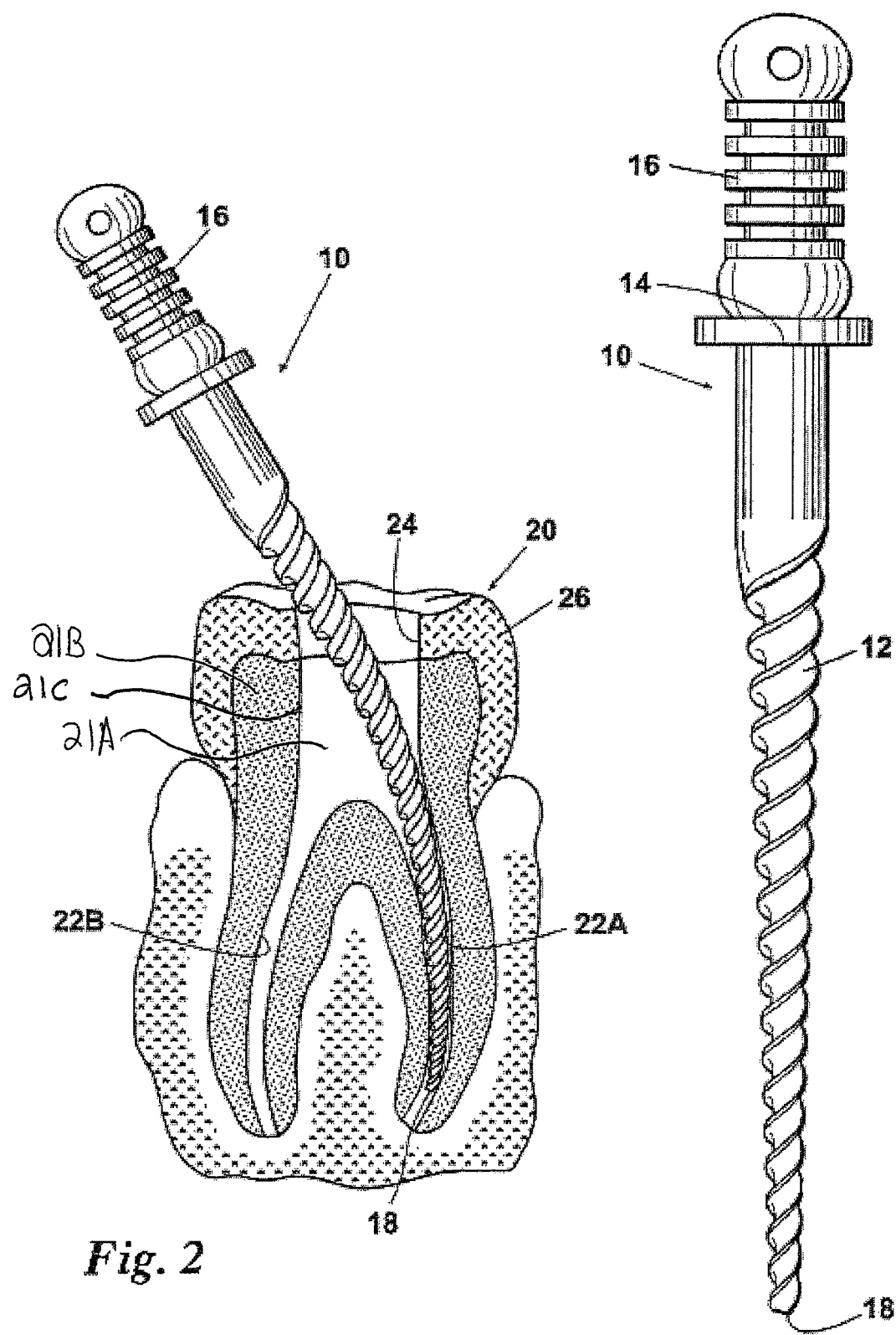

Referring to the drawings, FIGS. 1A-1C show elevational views of typical dental instruments generally indicated by the numeral 10A, 10B, and 10C used for shaping and/or cleaning root canals of a tooth. FIG. 2 shows the endodontic instrument of FIG. 1A being positioned within one of the root canals of a tooth. While in this position, the endodontic instrument is typically subjected to substantial cyclic bending and torsional stresses as it is used in the process of cleaning and shaping a root canal.

An endodontic file is a good example of a product that is subject to fatigue failure and wherein a failure of the product is a serious event. The endodontic files 10A, 10B, and 10C, each generally have an elongated shaft portion 12 with a proximal end 14 to which may be secured to a handle 16 (normally made of plastic) as shown in FIG. 1A, or which may be secured to an attachment end 17 for attachment to a handpiece (e.g., a rotary device) as shown in FIGS. 1B and 1C. The file shaft portion 12 (e.g., working portion) is configured to be inserted into and removed from the root canal of the tooth. As shown in FIGS. 1A-1C, endodontic files may be formed having different lengths and/or various file tapers. More particularly, the distal end 18 of files 10A and 10C have a reduced diameter compared to the proximal end 14 and is typically pointed. For example, it is appreciated that the diameter may be reduced so that the shaft portion 12 includes greater than about 0% taper, preferably from about 1% to about 10% taper, and most preferably from about 2% to about 6% taper. However, as shown in FIG. 1B, it is further appreciated that the shaft portion 12 may include about 0% taper while still having a reduced diameter at the distal end 18 (e.g., tip) of file 10B.

As defined herein, the file length refers to the length of the shaft from the proximal end to the tip of the file in a normal state relative to the file axis (e.g., the distance along the file axis from the proximal end to the tip of the file). Shaft length refers to the actual length of the shaft from the proximal end to the tip of the file in a normal state (e.g., the distance along the shaft from the proximal end to the tip of the file). For example, a nonlinear file will generally have a shaft length that may be greater than its file length in a normal state (due to the curved portions) while a linear file will generally have a shaft length that may be generally the same as its file length in a normal state.

FIG. 2 illustrates a typical tooth 20, in this case is a molar, having plural roots 22A and 22B, which in a healthy tooth are filled with pulpal material 21A being generally surrounded by dentin 21B with a dentin/pulpal interface therebetween 21C. The dentin/pulpal interface generally defining the root canals 22A and 22B. When this pulpal material becomes infected the tooth is deemed to be abscessed and the pressure generated by the abscess causes an intense tooth ache. Endodontists treat this malady by performing a root canal procedure in which the root canals 22A and 22B are cleaned of pulpal material. To do that a hole 24 is drilled in the tooth crown 26 to provide access to the root canals 22A and 22B. An endodontist inserts a file 10 through the hole 24 into the canals to facilitate removal of the pulpal material. FIG. 2 shows the tooth free of pulpal material.

The endodontic tools 10A-10C of FIGS. 1A-1C and 2 are, as previously stated, an example of a type of instrument that requires a high degree of flexibility along with resistance to cyclic fatigue and torsional loading. It can be seen that if in the process of treating a root canal 22A a lower portion of dental file 10A-10C is broken off in the canal then the endodontist is faced with a serious problem, particularly if the root canal beneath the broken off portion has not been thoroughly cleaned of infected pulpal material. It is therefore important in manufacturing endodontic files to provide files that have great flexibility and at the same time high fatigue resistance.

It is important to understand that the endodontic file shown in FIGS. 1A-1C and 2 and the use thereof is by example only to establish the need for structural material for use in constructing the shaft portion 12 to achieve high flexibility and, most importantly, high fatigue resistance. It is important to understand that the invention herein does not concern endodontic files per se but concerns methods of treating material, and particularly treating an alloy to produce a metal having ideal characteristics for use in the manufacture of endodontic tools and other similar medical and non-medical devices that require high fatigue resistance.

Non-superelastic Instrument and Methods of Manufacturing Thereof

The present invention includes an instrument (e.g., endodontic file) made of shape memory alloys in their martensitic state, and methods for manufacturing thereof. The martensitic state of the non-superelastic file may allow for more flexibility and increased fatigue resistance through an optimized microstructure while effectively shaping and cleaning root canals.

A Shape Memory Alloy is an alloy that "remembers" its original shape that is capable of returning to its predeformed shape by heating. More particularly, a desirable characteristic of the shape memory alloy (e.g., NiTi based alloy) in the "shape memory" form (or martensitic state), may be the temperature above which the bent materials will become straight again. For example, you may need to heat the material above its austenite finish temperature ($A_f$) to achieve its predeformed shape (e.g., a completely straight position).

Shape memory alloys may be considered superelastic at this "application" temperature (e.g., temperature above $A_f$) once they are capable of returning to their original shape (e.g., predeformed shape such as its original straight position, original curved position or otherwise). Furthermore, cooling (e.g., using dry ice, liquid nitrogen, or otherwise) the SMA material in a deformed shape (e.g., bending the material), the material may remain in the deformed position. Once the SMA material is removed from the cold environment, the material will return to a straight form at room temperature.

Desirably, martensite may be the primary metallurgical phase in the present invention instrument, which is different from standard NiTi rotary instruments with predominant austenite structure at ambient temperature. It is appreciated that the martensitic phase may be present in an amount greater than 0%, preferably greater than about 25%, and preferably greater than about 50% at ambient temperature. Furthermore, the martensitic phase may be present in an amount between about 25% and about 100%, preferably between about 50% and about 100%, and most preferably between about 75% and about 100% at ambient temperature. It is further appreciated that the martensitic phase may be the only phase present (e.g., M phase) at ambient temperature, though not required.

Optionally, the austenite phase may be present at ambient temperature. When included, the austenite phase may be present as an inner region (e.g., core region of the instrument) that may be generally surrounded by the martensite phase as an exterior layer (e.g., surface layer of the instrument) at ambient temperature. It is also appreciated that the martensite phase and the austenite phase, when included) may be present dispersed variably throughout the instrument at ambient temperature.

It is believed that typical superelastic NiTi rotary instruments have austenite finish temperatures lower than ambient temperature (25° C.). Desirably, in one embodiment of the present invention, a non-superelastic file may be provided having a higher austenite finish temperature (the final $A_f$ temperature measured by Differential Scanning calorimetry) than the ambient temperature (25° C.). More particularly, the austenite finish temperature may at least about 3° C., at least about 5° C., at least about 7° C., preferably at least about 10° C., and more preferably at least about 12° C. higher than the ambient temperature (25° C.). Furthermore, it is appreciated that the austenite finish temperature may less about 60° C., less than about 50° C., preferably less than about 40° C., and more preferably less than 38° C. For example, the austenite finishing temperature may range from about 28° C. to about 60° C., from about 30° C. to about 50° C., preferably from about 32° C. to about 40° C. and more preferably from about 35° C. to about 38° C. or from about 37° C. to about 40° C.

Due to higher austenite finish temperature, the present invention instrument may not completely return to the original shape (e.g., straight state) after being bent or deflected. This is in contrast to the conventional superelastic NiTi rotary instruments having an, which may return to its original shape (e.g., straight state) via reverse phase transformation (martensite-to-austenite) upon unloading due to the $A_f$ of the convention instrument being lower than ambient temperature.

Endodontic instruments made of NiTi shape memory alloys in martensitic state (e.g., non-superelastic state may have increased overall performance relative to their austenitic counterparts (e.g., conventional superelastic NiTi instruments), especially on flexibility and resistance against cyclic fatigue.

The strength and cutting efficiency of endodontic instruments may be improved by providing ternary shape memory alloys NiTiX (X: Co, Cr, Fe, Nb, etc) based on the mechanism of alloy strengthening in a non-superelastic state.

Specifically, in one embodiment of the present invention, non-superelastic instrument has improved and desired characteristics for successful root canal surgery, including higher flexibility and lower stiffness, improved resistance to cyclic fatigue, higher degree of rotation against torsional fracture, more conforming to the shape of highly curved canals (less likely for ledging or perforation), minimum possibility of instrument separation, and/or otherwise in comparison against conventional endodontic instruments formed of a shape memory alloy in superelastic condition (e.g., in a fully austenitic phase in microstructure) and/or being generally linearly shaped.

In one embodiment of the present invention, endodontic instruments made of shape memory alloys (e.g., NiTi) in their martensitic state (non-superelastic state) may be fabricated by the one of the following method described herein.

One method (e.g., Method 1) of forming a non-superelastic file may comprise the steps of post heat treating a file (e.g., the flutes of a file shaft) after being manufactured according to a predetermined mechanical design (i.e., after the flute grinding process in a typical file manufacturing process).

This method for forming the non-superelastic instrument may include a post heat treatment having a heating step at temperature of at least about 300° C., at least about 350° C., preferably at least about 400° C., and more preferably at least about 450° C. Furthermore, it appreciated that the heating step may include heating to a temperature less than about 650° C., less than about 600° C., preferably less than 550° C., and more preferably less 525° C. For example, the heating step may include heating to a temperature ranging from about 300° C. to about 650° C. (e.g., from about 300° C. to about 600° C.), from about 350° C. to about 600° C. (e.g., from about 370° C. to about 510° C.), preferably from about 400° C. to about 550° C., and more preferably from about 450° C. to about 525° C.

The heat treatment process for forming a shape-set nonlinear file may include heating a superelastic file to a temperature for a time period of at least about 1 minute, preferably at least about 3 minutes, and more preferably at least about 5 minutes to shape-set the superelastic file thereby forming a shape-set nonlinear file. Furthermore, it is appreciated that the heat treatment process for forming a shape-set nonlinear file may include heating a superelastic file to a temperature for a time period of less than about 45 minutes, preferably less than about 30 minutes, and more preferably less than about 20 minutes. For example, the heat treatment process for forming a shape-set nonlinear file may include heating a superelastic file to a temperature for a time period from about 1 minute to about 45 minutes, preferably from about 3 minutes to about 30 minutes, and more preferably from about 5 minutes to about 20 minutes.

The heat treatment process for forming a non-superelastic instrument may include heating the superelastic instrument for a time period of at least about 5 minutes, preferably at least about 30 minutes, and more preferably at least about 40 minutes. Furthermore, it is appreciated that the heat treatment process for forming a non-superelastic instrument may include heating the superelastic instrument for a time period less than about 200 minutes, preferably less than about 120 minutes, and more preferably less than about 90 minutes. For example, the heat treatment process for forming a non-superelastic instrument may include heating the superelastic instrument for a time period from about 5 minutes to about 200 minutes (e.g., from about 5 minutes to about 120 minutes or from about 10 minutes to about 60 minutes), preferably from about 30 minutes to about 120 minutes, and more preferably from about 40 minutes to about 90 minutes (e.g., from about 40 minutes to about 70 minutes). Typically the heating step occurs under a controlled atmosphere. Preferably, the controlled atmosphere may include (e.g., consist) a reactive gas (e.g., oxygen, air, or otherwise), though not required. When included, the reactive gas such as air reacts with the surface of the instrument so that an oxidation layer (e.g., blue oxidation layer) may be formed. Optionally, the controlled atmosphere may include (e.g., consist) a nonreactive gas (e.g., helium neon, argon, krypton, xenon, and/or radon).

As mentioned above, the post heat treatment step (e.g., additional thermal process) of Method 1 may be employed after the traditional NiTi rotary file manufacturing process (e.g., grinding of the flutes) using regular superelastic NiTi wires. More particularly, an additional thermal process may be performed after the flute grinding process (of a traditional NiTi rotary file manufacturing process) so that a post heat treatment occurs at a temperature range of 370~510° C. for a period of time (typically 10-60 min, depending on file size, taper, and/or file design requirement). It is appreciated that Nickel-rich precipitates may form during this post heat treatment process. Correspondingly, the ratio of Ti/Ni may increase and a desired austenite finish temperature (the final $A_f$ temperature) will be achieved. After post heat treatment, a file handle (e.g., brass, steel, the like, or otherwise may be installed.

In another embodiment of the present invention, endodontic instruments made of shape memory alloys (e.g., NiTi) in their martensitic state (non-superelastic state) may be fabricated by the one of the following method described herein.

Another method (e.g., Method 2) of forming a non-superelastic instrument may comprise the steps of post heat treating a file (e.g., the flutes of a file shaft) during the manufacturing of the superelastic instrument (e.g., during the grinding process) so that the temperature of the instrument may be higher than the austenite finish temperature.

This method may include (concurrent) heat treatment to SMA wire(s) prior to and/or during the grinding process so that grinding may be directly applied to martensitic SMA (e.g., NiTi) wires. However, it is appreciated that martensitic SMA (e.g., NiTi) wires may be heated to a temperature higher than their austenite finish temperatures during grinding process. Therefore, martensitic SMA (e.g., NiTi) wires may temporarily transform to superelastic wires (a stiffer structure in the austenitic state) to facilitate the grinding process during the instrument manufacturing process. Advantageously, the instruments may transform back to martensitic state at ambient temperature after the flute grinding process.

For example, in one embodiment, Method 2 may include a non-superelastic wire. The non-superelastic wire may be provided in a manufacturing environment with a temperature higher than its austenite finish temperature (at least 25 degree C.). The non-superelastic wire may transform to superelastic at this higher temperature). Then forming flutes and grooves about the file to form the (semi finished) rotary file. Furthermore, the (semi-finished) rotary file may be removed from the manufacturing environment with higher (warmer) temperature. The non-superelastic wire may form a non-superelastic rotary file at (or above) room temperature about 25° C.

It is believed that a shape memory alloy like NiTi alloy generally has two primary crystallographic structures, which are temperature dependent, (i.e. austenite at higher temperatures and martensite at lower temperatures). This temperature-dependent diffusionless phase transformation will be from martensite (M) to austenite (A) (e.g., M→A) during heating. Furthermore, it is appreciated that a reverse transformation from austenite to martensite (A→M) may be initiated upon cooling. In another embodiment, an intermediate phase (R) may appear during phase transformations i.e., either (M)→(R)→(A) during heating or (A)→(R)→(M) during cooling. The R-phase being defined as an intermediate phase between the austenite phase (A) and the martensite phase (M). However, it is appreciated that during transformation both the martensite phase and the austenite phase may be present in addition to the optional R-Phase.

Figure 3:
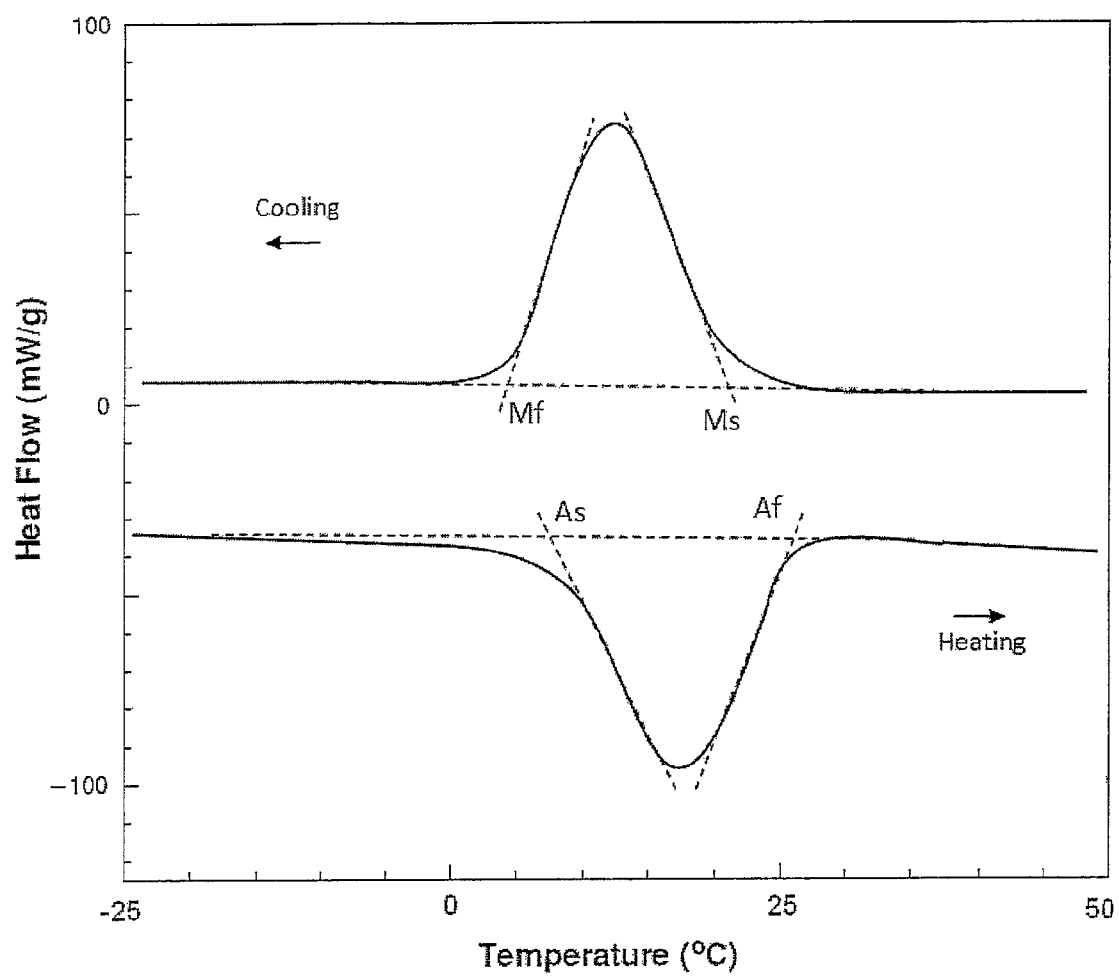
FIG. 3 is a Differential Scanning calorimetry (DSC) curve showing phase transformation temperatures of the present invention.

The phase transformation temperatures may be determined using Differential Scanning calorimetry (DSC) curve as shown in the FIG. 3. For example, $A_f$ (austenite finish temperature) may be obtained from the graphical intersection of the baseline with the extension of the line of maximum inclination of the peak of the heating curve. The final $A_f$ temperature of endodontic instrument made of shape memory alloys was measured in DSC test with general accordance with ASTM Standard F2004-05 "Standard Test Method for Transformation Temperature of Nickel-Titanium Alloys by Thermal Analysis", such as using heating or cooling rates of 10±0.5° C./min with purge gas of either helium or nitrogen, except that the fluted segment cut from rotary instrument sample does not need any further thermal annealing process (i.e., 850° C. for 30 min in vacuum), which is typically used for measuring ingot transition temperatures at fully austenitic condition.

More particularly, FIG. 3 provides a schematic differential scanning calorimetry (DSC) curve of a shape memory alloy (nickel-titanium) in both heating and cooling cycle. $A_f$ (austenite finish temperature), $A_s$ (austenite start temperature), $M_f$ (martensite finish temperature), $M_s$ (martensite start temperature) may be obtained from the graphical intersection of the baseline with the extension of the line of maximum inclination of the appropriate peak of the curve. The martensite start temperature ($M_s$) being defined as the temperature at which the transformation from austenite to martensite begins on cooling. The martensite finish temperature ($M_f$): the temperature at which the transformation from austenite to martensite finishes on cooling; Austenite start temperature ($A_s$) being defined as the temperature at which the transformation from martensite to austenite begins on heating. The austenite finish temperature, ($A_f$) being defined as the temperature at which the transformation from martensite to austenite finishes on heating.

Experimental results have shown that the present invention (e.g., an additional heat treatment process for the formation of endodontic instruments) results in desirable characteristics. More particularly, the endodontic instruments made of NiTi shape memory alloys in their martensitic state may include one or more of the following desired characteristics for root canal surgery: (1) higher flexibility and lower stiffness; (2) improved resistance to cyclic fatigue; (3) higher degree of rotation against torsional fracture; (4) more conforming to the curved canal profile, especially for the root canals with considerable curvature and complex profile, and combinations thereof relative to conventional superelastic instruments of similar shape and/or size.

For example in order to compare the impact of different metallurgical structures (austenite vs. martensite), two different instrument samples were made utilizing different thermal processing in order to represent two distinct structures: (1) superelastic instruments with fully austenitic microstructure and (2) instrument with martensitic microstructure. In one specific example based on the DSC measurements, the final $A_f$ temperatures for these two instruments with distinct microstructures are 17° C. (for instrument (1) having the fully austenitic microstructure) and 37° C. (for instrument (2) having the martensitic microstructure), respectively. All instrument samples were of the same geometric design. All tests were performed at ambient temperature ~23° C.

I. Stiffness test: Showing higher flexibility and lower stiffness on endodontic instruments made of NiTi shape memory alloys in their martensitic state as compared to NiTi shape memory alloys in their austenitic state.

Figure 4:
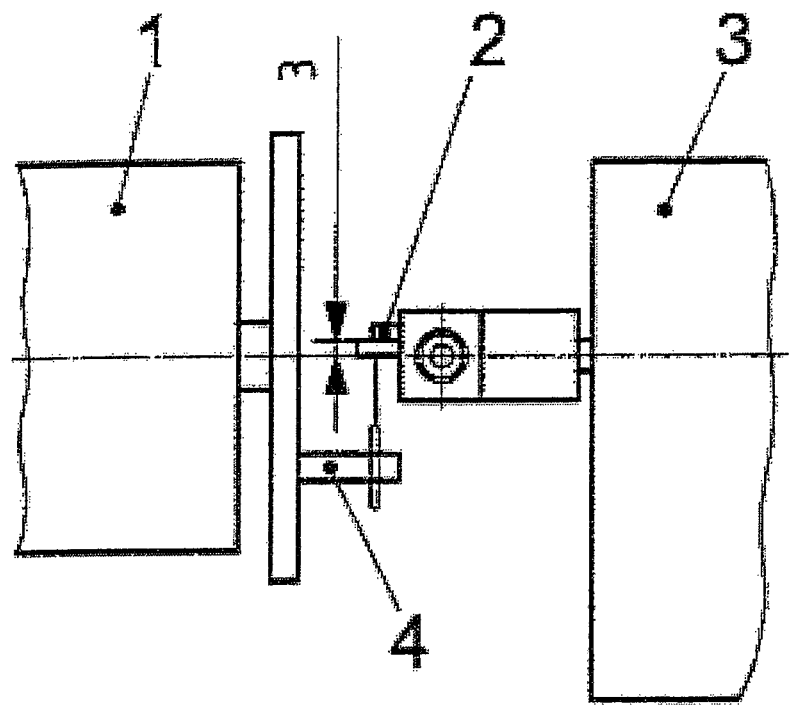
FIG. 4 is a diagrammatic representation of a bending test apparatus to measure stiffness of root canal instruments as described in ISO 3630-1:2008, Dentistry—Root-canal instrument—Part I: General requirements and test methods). The Apparatus for Bending Test includes a reversible gear 1', a stop 2', a torque-measuring device 3', and a catch pin 4'.

In this stiffness test, the stiffness of all sample instruments have been determined by twisting the root canal instrument through 45° using the testing apparatus as shown in FIG. 4.

Figure 5:
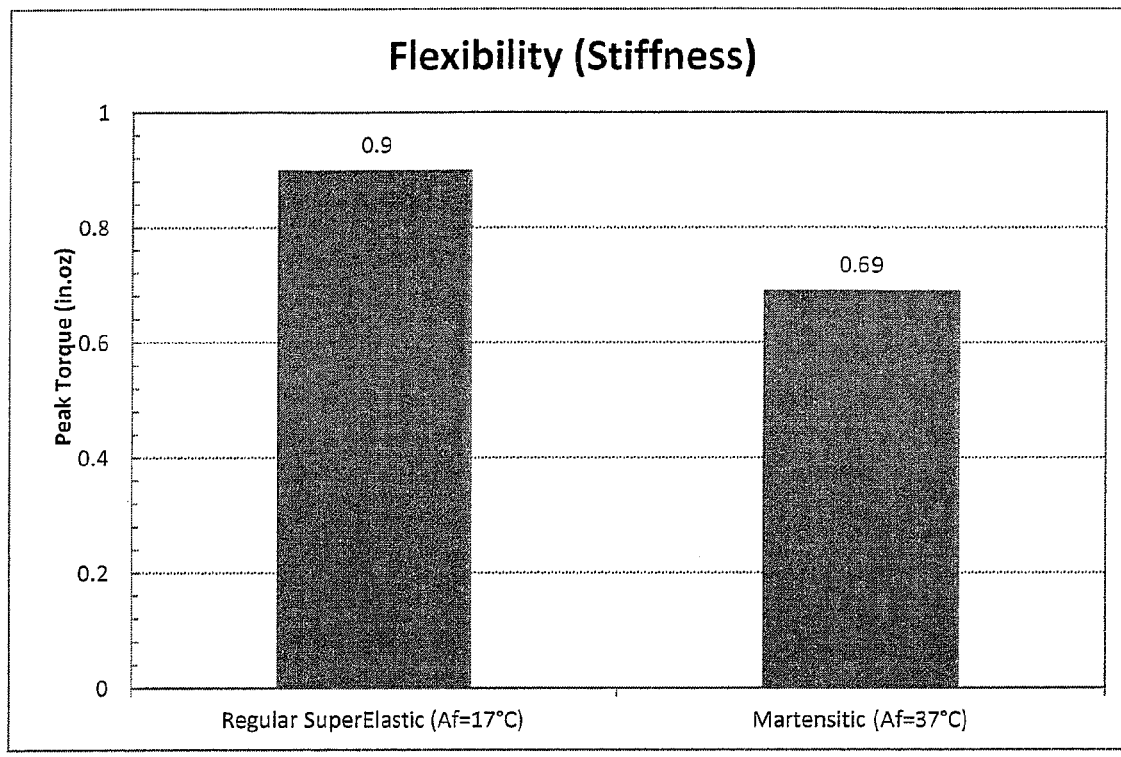
FIG. 5 is a chart showing the testing results of the test method shown in FIG. 4.

As shown in the testing results in FIG. 5, the rotary instruments with martensitic microstructure at ambient temperature exhibit higher flexibility and lower stiffness (as indicated by lower peak torque on bending). In comparison with the regular superelastic instrument with the final $A_f$ temperature 17° C., the instruments with the martensitic microstructure (the final $A_f$ temperature ~37° C.) have shown 23% reduction in bending torque. The lower stiffness of martensitic instruments can be attributed to the lower Young's modulus of martensite (about 30~40 GPa) whereas austenite is about 80~90 GPa at ambient temperature.

FIG. 5 shows a schematic graph of the relationship between different NiTi microstructures (regular superelastic or austenic vs. martensitic) and average peak torque of endodontic rotary instruments made of NiTi shape memory alloy in bending test. As can gleemed from FIG. 5, lower peak torque (less stiff or more flexible) may be achieved by a martensitic microstructure, which is indicated by the higher $A_f$ (austenite finish temperatures). In one embodiment, the ratio of peak torque (flexibility/stiffness) of the non-superelastic rotary file to the superelastic rotary file may be less than about 1:0.9 (e.g., less than about 1:0.85, and preferably less than about 1:0.8) at about 25° C.

Figure 6:
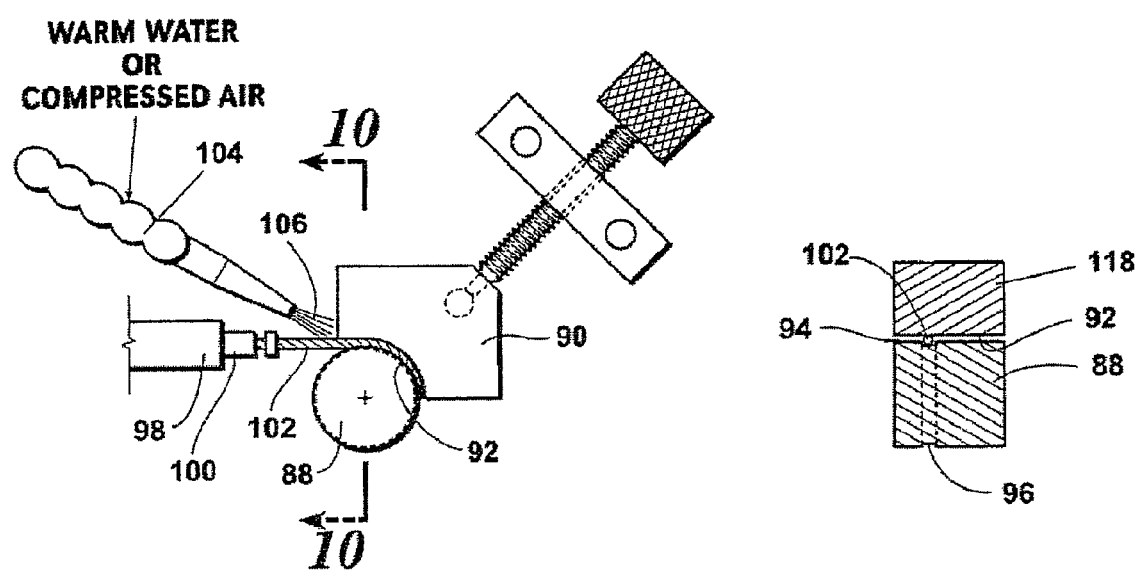
FIG. 6 is diagrammatic representation of a test apparatus used to test the bending-rotation fatigue resistance of endodontic instruments.

II. Bending rotation fatigue test: Showing higher fatigue life on endodontic instruments made of NiTi shape memory alloys in their martensitic state In this bending test, the fatigue resistance of all sample instruments is measured by bending rotation fatigue tester as shown in FIG. 6. According to the testing results shown in FIG. 7, the average cyclic fatigue life of instruments in the martensitic state ($A_f$ temperature 37° C.) is about 3 times of its austenitic counterpart ($A_f$ temperature 17° C.).

As shown in the diagrammatic representation of FIG. 6, a test apparatus may be used to test the bending-rotation fatigue resistance of endodontic instruments. The endodontic rotary instrument sample may be generally rotating freely within a simulated stainless steel canal with controlled radius and curvature.

Figure 7:
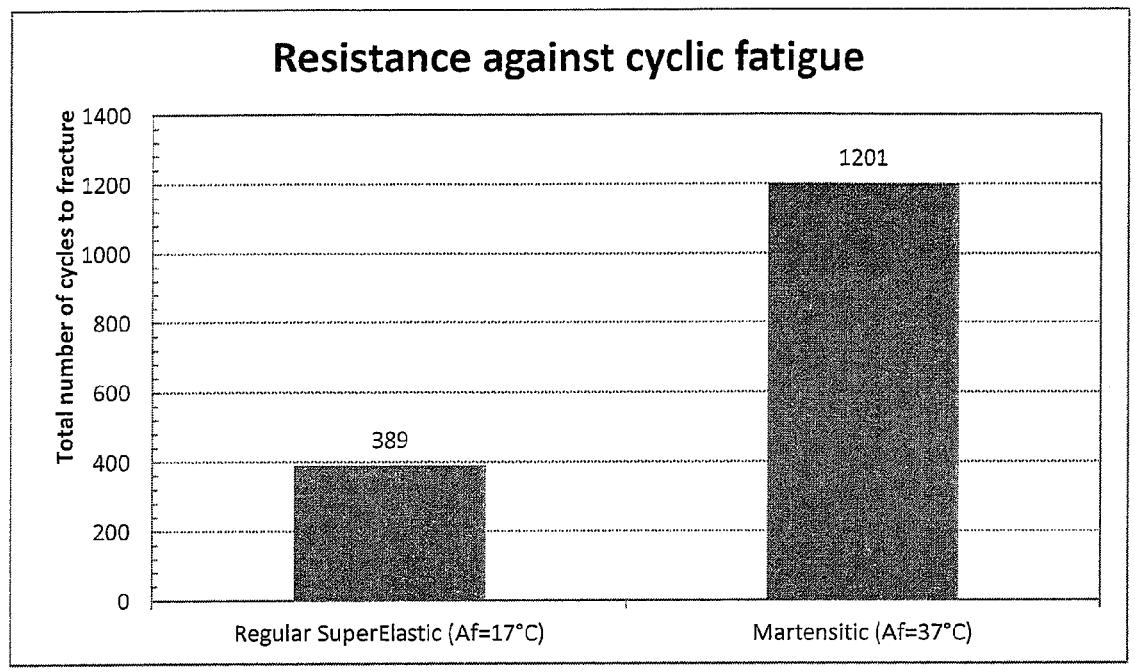
FIG. 7 is a schematic graph of the relationship between different NiTi microstructures (austenic vs. martensitic) and average cyclic fatigue life of endodontic rotary instruments made of NiTi shape memory alloy.

The schematic graph of FIG. 7 shows the relationship between different NiTi microstructures (austenic vs. martensitic) and average cyclic fatigue life of endodontic rotary instruments made of NiTi shape memory alloy. More particularly, FIG. 7 shows that longer cyclic fatigue life may be achieved by a martensitic microstructure at ambient temperature, which is indicated by the higher $A_f$ (austenite finish temperature). It is appreciated that the ratio of total number of cycles to fatigue (resistance against cyclic-fatigue) of the non-superelastic rotary file to the superelastic rotary file may be at least about 1.25:1 (e.g., at least about 1.5:1, preferably at least about 2:1) at about 25° C.

Figure 8:
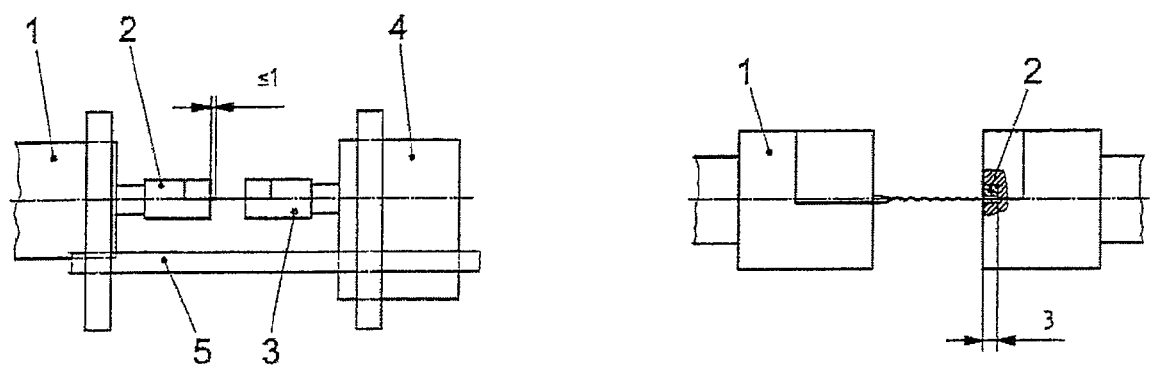
FIG. 8 is a diagrammatic representation of a torque test apparatus used to measure the resistance to fracture by twisting and angular deflection as described in ISO 3630-1:2008, Dentistry—Root-canal instrument—Part I: General requirements and test methods). The Apparatus for Torque Test includes a reversible gear motor 1", a chuck with hardened steel jaws 2", a chuck with soft brass jaws 3", a torque measuring device 4", and a linear ball-bearing 5". The Apparatus for Torque Test further includes Details of the Test Chuck, which includes a chuck with hardened steel jaws 1''' and a soft brass

III. Torque test: Showing higher degree of rotation against torsional fracture on endodontic instruments made of NiTi shape memory alloys in their martensitic state In this torque test, the resistance to fracture of root canal instruments is performed to measure the average maximum degree of rotation against torsional fracture using the testing apparatus as shown in FIG. 8. According to the testing results in FIGS. 9 and 10, the instruments with a martensitic microstructure exhibit a higher degree of rotation and peak torque against torsional fracture than their austenitic counterparts.

It is appreciated that most instrument separation may have been caused by either cyclic fatigue or torsional fracture;

therefore, the separation of instruments made of shape memory alloys with martensitic microstructure may be significantly reduced according to the testing results in (II) bending rotation fatigue test and (III) torque test.

Figure 9:
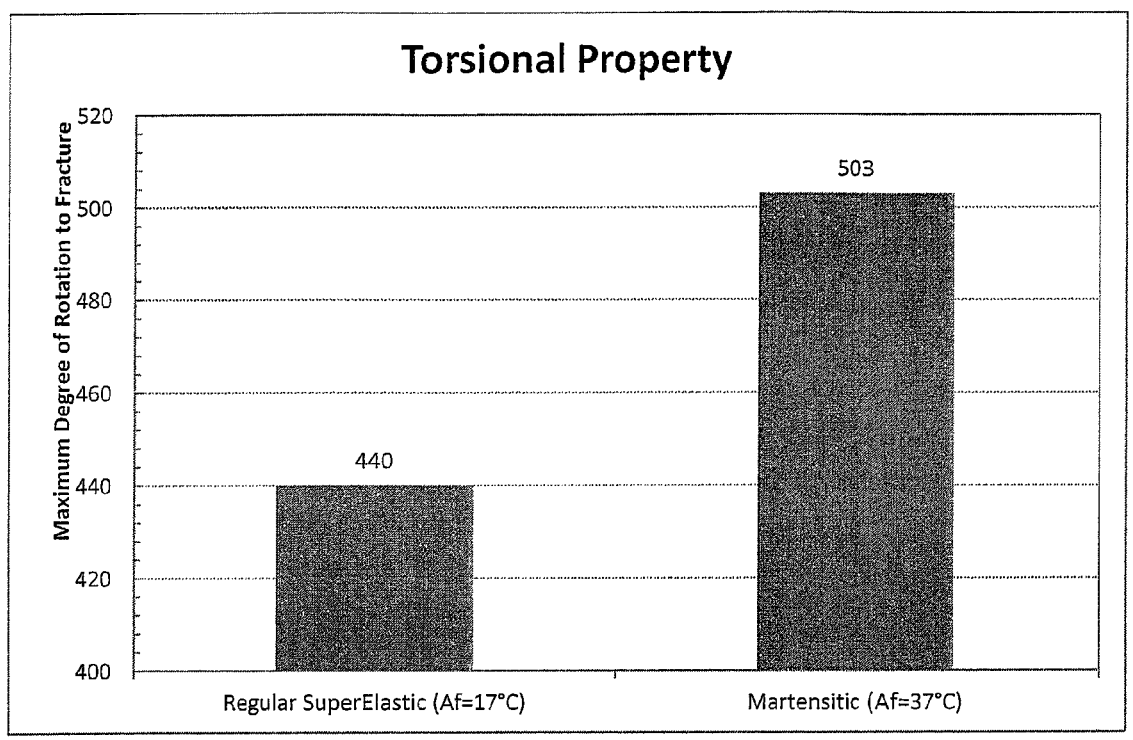
FIG. 9 is a schematic graph of the relationship between different metallurgical structures and average "maximum degree of rotation to fracture" of endodontic rotary instruments made of NiTi shape memory alloy.

The schematic graph of FIG. 9 shows the relationship between different metallurgical structures and average "maximum degree of rotation to fracture" of endodontic rotary instruments made of NiTi shape memory alloy. More particularly, FIG. 9, shows that a higher degree of rotation may be achieved by martensitic microstructure. It is appreciated that the ratio of the maximum degree of rotation to fracture (torsional property) of the non-superelastic rotary file to the superelastic rotary file may be at least about 1.05:1 (e.g., at least about 1.075:1, preferably at least about 1.1:1) at about 25° C.

Figure 10:
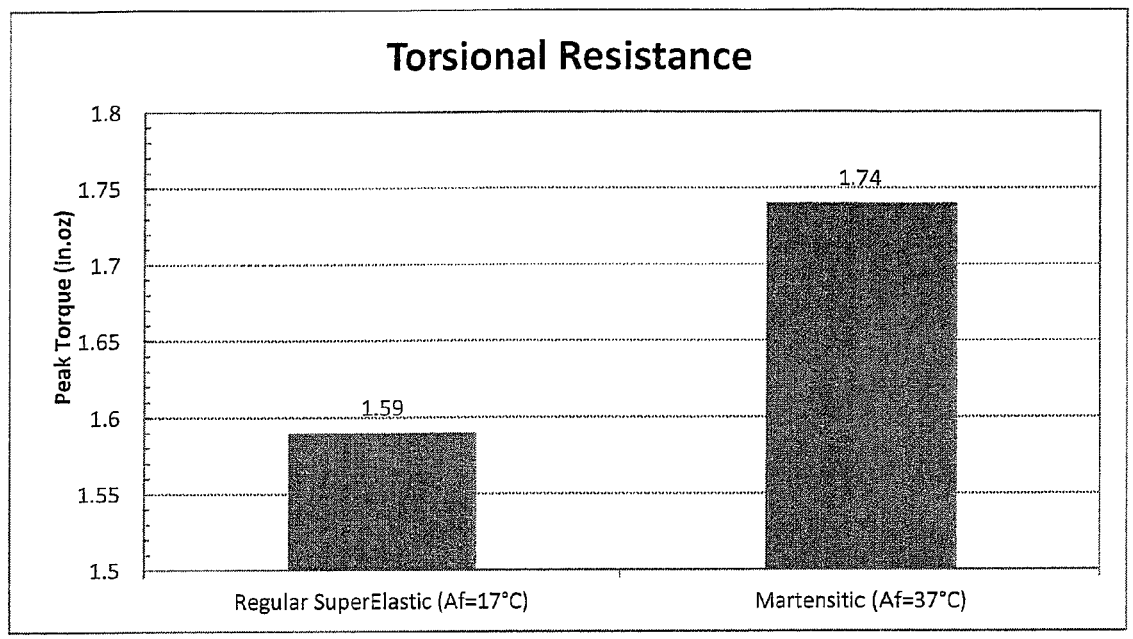
FIG. 10 is a schematic graph of the relationship between different metallurgical structures and average "peak torque" of endodontic rotary instruments made of NiTi shape memory alloy.

The schematic graph of FIG. 10 shows the relationship between different metallurgical structures and average "peak torque" of endodontic rotary instruments made of NiTi shape memory alloy. More particularly, FIG. 10, shows that higher torque resistance may be achieved by a martensitic microstructure. It is appreciated that the ratio of peak torque (torsional resistance) of the non-superelastic rotary file to the superelastic rotary file may be at least about 1.05:1 (e.g., at least about 1.075:1, preferably at least about 1.09:1) at about 25° C.

IV. Endodontic instruments made of NiTi shape memory alloys in their martensitic state show increased conforming to a curved canal profile relative to conventional superelastic instruments of similar shape and/or size.

Figure 11:
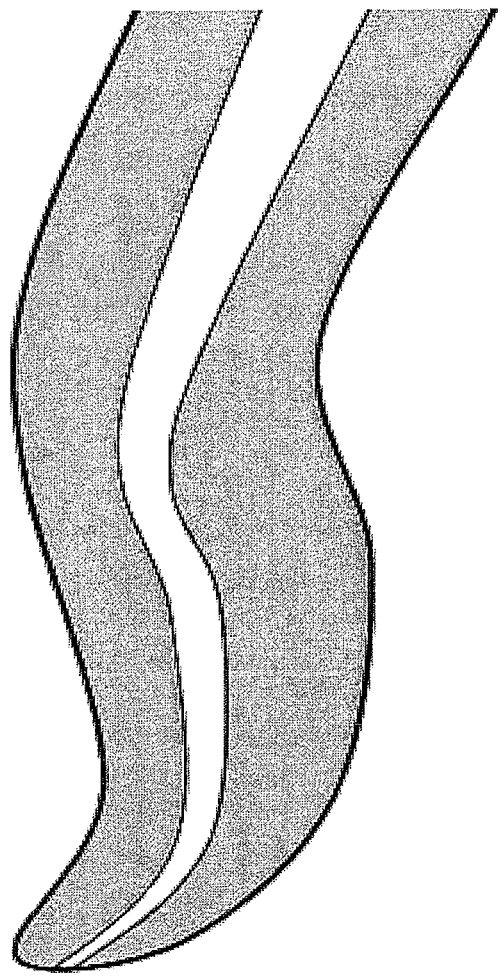
FIG. 11 shows a root with a highly curved canal and a complex canal shape.

Without introducing ledging, transportation, and/or perforation, it is appreciated that instruments formed of shape memory alloys in their martensitic microstructure may be used in cleaning and shaping the highly curved canal as shown in FIG. 11. Advantageously, these instruments tend to be more conforming to the curvature of the root canal because of (1) high flexibility due to the presence of martensite; (2) better reorientation and self-accommodation capability of the martensitic variants due to the low symmetry of monoclinic crystal structure of martensite relative to the cubic crystal structure of austenite under applied dynamic stresses during root canal surgery.

A secondary heat treatment may be utilized to further control the stiffness of the non-superelastic file by providing one or more bends therein while optimizing the material properties of the file. This may be accomplished by heat treating the non-superelastic file at certain parameters to adjust the stiffness of the file (e.g., making the non-superelastic file stiffer or less stiff. For example, in one embodiment, a shape set non-superelastic nonlinear file may be formed by further heat treating a non-superelastic file using the heat treatment method described herein of forming a shape set nonlinear file, though not required. It is appreciated that the heat treatment process for forming a shape-set nonlinear file (e.g., as discussed below) may generally include positioning the non-superelastic file within a fixture so that the non-superelastic file may be orientated into a nonlinear file path and heating the fixture including the non-superelastic file to a temperature from about 300° C. to about 650° C. (e.g., about 450° C. to about 550° C.) for a period of time from about 1 minutes to about 45 minutes (e.g., about 3 minutes to about 30 minutes, and preferably about 5 minutes to about 20 minutes) thereby shape-setting the non-superelastic file to form a shape-set non-superelastic nonlinear file when utilized after the non-superelastic heat treatment process.

It can be seen that the invention can also be described with reference to one or more of the following combinations.

A. A method for manufacturing a non-superelastic rotary file comprising the steps of: (i) providing a superelastic rotary file having an austenite finish temperature; and (ii) heating the superelastic rotary file to a temperature of at least about 300° C. for a time period of at least about 5 minutes to alter the austenite finish temperature thereby forming the non-superelastic rotary file; wherein the altered austenite finish temperature of the non-superelastic rotary file is greater than about 25° C.

B. The method of claim 1, wherein the altered austenite finish temperature of the non-superelastic rotary file is greater than 27° C. (e.g., between about 27° C. and 35° C.).

C. The method of claim 1 or 2, wherein the altered austenite finish temperature of the non-superelastic rotary file is greater than 30° C. (e.g., between about 30° C. and 35° C.).

D. The method of any of the preceding claims, wherein the altered austenite finish temperature of the non-superelastic rotary file is greater than 33° C. (e.g., between about 33° C. and 35° C.).

E. The method of any of the preceding claims, wherein the altered austenite finish temperature of the non-superelastic rotary file is greater than 35° C. (e.g., between about 35° C. and 40° C.).

F. The method of any of the preceding claims, wherein the altered austenite finish temperature of the non-superelastic rotary file is greater than 37° C. (e.g., between about 37° C. and 45° C.).

G. The method of any of the preceding claims, wherein the heating step, the temperature ranges from about 300° C. to about 600° C.

H. The method of any of the preceding claims, wherein the heating step, the temperature ranges from about 370° C. to about 510° C.

I. The method of any of the preceding claims, wherein the heating step, the time period ranges from about 5 minutes and about 120 minutes.

J. The method of any of the preceding claims, wherein the heating step, the time period ranges from about 10 minutes and about 60 minutes.

K. The method of any of the preceding claims, wherein the superelastic rotary file includes a shape memory alloy.

L. The method of any of the preceding claims, wherein the shape memory alloy includes nickel and titanium.

M. The method of any of the preceding claims, wherein the shape memory alloy is a nickel-titanium based binary alloy.

N. The method of any of the preceding claims, wherein the shape memory alloy is a nickel-titanium based ternary alloy.

O. The method of any of the preceding claims, wherein the nickel-titanium based ternary alloy of the formula Ni—Ti—X wherein X is Co, Cr, Fe, or Nb P. The method of any of the preceding claims, wherein the shape memory alloy includes a copper based alloy, an iron based alloy or a combination of both.

Q. The method of any of the preceding claims, wherein the shape memory alloy is the copper based alloy includes CuZnAl or CuAlNi.

R. The method of any of the preceding claims, wherein the shape memory alloy is the iron based alloy includes FeNiAl, FeNiCo, FeMnSiCrNi, or FeNiCoAlTaB.

S. The method of any of the preceding claims, wherein the ratio of peak torque (flexibility/stiffness) of the non-superelastic rotary file to the superelastic rotary file is less than about 8:9 at about 25° C.

T. The method of any of the preceding claims, wherein the ratio of total number of cycles to fatigue (resistance against cyclic fatigue) of the non-superelastic rotary file to the superelastic rotary file is at least about 1.25:1 at about 25° C.

U. The method of any of the preceding claims, wherein the ratio of maximum degree of rotation to fracture (torsional property) of the non-superelastic rotary file to the superelastic rotary file is at least about 1.05:1 at about 25° C.

V. The method of any of the preceding claims, wherein the ratio of peak torque (torsional resistance) of the non-superelastic rotary file to the superelastic rotary file is at least about 1.05:1 at about 25° C.

W. The method of any of the preceding claims, further comprising the step of providing a handle and attaching the handle to a portion of the non-superelastic rotary file.

X. The method of any of the preceding claims, wherein for binary NiTi, the nickel weight percentage may range from about 45% to about 60% (e.g., about 54.5% to about 57%) with a balance of titanium composition being about 35% to about 55% (e.g., about 43% to about 45.5%).

Y. The method of any of the preceding claims, wherein for ternary NiTiX, the X element may be less than 15% (e.g., less than about 10%) in weight percentage.

Z. A method for manufacturing a non-superelastic rotary file comprising the steps of (i) providing a non-superelastic wire having an austenite finish temperature greater than about 25° C.; (ii) heating the non-superelastic wire to a manufacturing temperature that is higher that the austenite finish temperature; and (iii) forming flute(s), groove(s), or a combination of both about the superelastic wire to form a rotary file; wherein the rotary file is non-superelastic at a temperature that ranges from about 25° C. to about the austenite finish temperature.

AA. The method of claim 23, wherein the austenite finish temperature of the non-superelastic rotary file is greater than 26° C. (e.g., between about 26° C. and 35° C.).

BB. The method of claim 23, wherein the austenite finish temperature of the non-superelastic rotary file is greater than 27° C. (e.g., between about 27° C. and 35° C.).

CC. The method of claim 23 or 24, wherein the austenite finish temperature of the non-superelastic rotary file is greater than 30° C. (e.g., between about 30° C. and 35° C.).

DD. The method of any of the preceding claims, wherein the austenite finish temperature of the non-superelastic rotary file is greater than 33° C. (e.g., between about 33° C. and 40° C.).

EE. The method of any of the preceding claims, wherein the austenite finish temperature of the non-superelastic rotary file is greater than 35° C. (e.g., between about 35° C. and 40° C.).

FF. The method of any of the preceding claims, wherein the austenite finish temperature of the non-superelastic rotary file is greater than 37° C. (e.g., between about 37° C. and 45° C.).

GG. The method of any of the preceding claims, wherein the heating step, the manufacturing temperature ranges from about 5° C. to about 200° C.

HH. The method of any of the preceding claims, wherein the heating step, the manufacturing temperature ranges from about 10° C. to about 50° C.

II. The method of any of the preceding claims, wherein the non-superelastic wire includes a shape memory alloy.

JJ. The method of any of the preceding claims, wherein the shape memory alloy includes nickel and titanium.

KK. The method of any of the preceding claims, wherein the shape memory alloy is a nickel-titanium based binary alloy.

LL. The method of any of the preceding claims, wherein the shape memory alloy is a nickel-titanium based ternary alloy.

MM. The method of any of the preceding claims, wherein the nickel-titanium based ternary alloy of the formula Ni—Ti—X wherein X is Co, Cr, Fe, or Nb NN. The method of any of the preceding claims, wherein the shape memory alloy includes a copper based alloy, an iron based alloy or a combination of both.

OO. The method of any of the preceding claims, wherein the shape memory alloy is the copper based alloy includes CuZnAl or CuAlNi.

PP. The method of any of the preceding claims, wherein the shape memory alloy is the iron based alloy includes FeNiAl, FeNiCo, FeMnSiCrNi or FeNiCoAlTaB.

QQ. The method of any of the preceding claims, further comprising the step of providing a handle and attaching the handle to a portion of the non-superelastic rotary file.

RR. The method of any of the preceding claims, wherein the handle is located distally from the flute(s), groove(s), or any combination thereof.

SS. A method for manufacturing a non-superelastic rotary file comprising the steps of providing a superelastic rotary file having an austenite finish temperature; and heating the superelastic rotary file to a temperature of at least about 300° C. for a time period of at least about 5 minutes to alter the austenite finish temperature thereby forming the non-superelastic rotary file; wherein the altered austenite finish temperature of the non-superelastic rotary file is greater than about 25° C.

Nonlinear Instruments and Methods of Manufacturing Thereof

The present invention further contemplates nonlinear instruments (e.g., endodontic instruments) and methods for forming thereof. A file design may be produced by utilizing a fixture to deflect portions of a conventional file (e.g., linear file) so that the geometry of the file may be arranged into a predetermined nonlinear finished shape and heating the file to form a shape-set nonlinear file. More particularly, shape setting a file to a desired geometry (e.g. generally nonlinear shape) to better distribute surface contact with the pulp material and/or infected material of the root canal relative to the wall of the root canal (e.g. dentin/pulp interface) during cleaning and/or shaping of root canals with various curvatures (e.g., extreme curvature). In one desirable aspect, the nonlinear shaped file may be configured to expand thereby ensuring the walls of the root canal are being cleaned (e.g., removing pulp and/or infected material) while minimizing the removal of dentin and/or pulp materials. In another desirable aspect, the nonlinear shaped file may be configured to collapse upon contact with one or more portions of the root canal walls when the root canal walls are narrower than the bends of the nonlinear shaped rotary file to reduce excessive removal of the dentin and/or pulp materials. Furthermore, the present invention may include the method of forming a nonlinear file, which may be accomplished by placing the conventional file into a fixture and then placing the fixture along with the file in a heated chamber for a time to shape set the file to the predetermined geometry thereby forming a shape-set nonlinear file.

FIGS. 12A, 12B, and 12C show various files (e.g. dental file) of the present invention having a nonlinear shape. Nonlinear files 20, 108, and/or 110 of FIGS. 12A-12C, respectively generally extend along a file axis 26 and include an elongated nonlinear shaft portion 22 having a tip 28, a proximal end 24 and a working portion therebetween. The proximal end 28 may be secured to a handle (not shown) or may include an attachment end 27 for attachment to a handpiece (e.g., a rotary device). The shaft 22 includes at least one offset portion 30 and preferably a plurality of offset portions 30 (e.g., bends) where at least a portion of the shaft 22 extends along an axis different from the file axis 26 thereby becoming generally nonlinear. In one preferred embodiment, the nonlinear shaft portion 22 extends within a common plane (e.g., in a two dimensional space).

It is appreciated that the nonlinear files may include a plurality of offsets 30 (e.g., at least about 2 offsets, at least about 3 offsets such as in nonlinear files 20 and 108, at least about 4 offsets such as nonlinear file 110, or otherwise). More particularly, the nonlinear file 20 may have a geometry similar to a generally C-shaped profile, a generally S-shaped profile, a generally sinusoidal shape profile or otherwise shaped nonlinear profile. It is appreciated that the nonlinear file may have a generally smaller shaft 22 length and/or a generally larger file taper as in nonlinear file 108 or may include a generally longer shaft 22 length and/or a generally smaller file taper as in nonlinear files 20 and 110, though not required. Optionally, the tip end 28 may be offset from the file axis 26 (FIGS. 12A and 12B) or may extend along the file axis 26 (FIG. 12C).

Generally, the offset portion 30 may include a section of the shaft 22 that generally extends between two locations along the file axis. For example, the offset portion may extend between a first shaft location 34A where the shaft begins to extend away from the file axis 26 and a second shaft location 34B where the shaft returns to the file axis 26. Furthermore, it is appreciated that the offset portion may extend from or to end portions of the shaft 22 (e.g., the tip 28, the proximal end 24, and/or otherwise). The offset portion 30 may include a crest 32. The crest 32 may be generally an outermost point within the corresponding offset portion 30 along the shaft portion 22 having the greatest distance from the file axis 26. This maximum distance (e.g., maximum displacement) between the crest 32 and the file axis 26 may be defined by the crest displacement distance 36.

In an embodiment having a plurality of offset portions 30, each offset portion 30 (e.g., 30A, 30B, etc. . . . ) may include a crest 32 (e.g., 32A, 32B, etc. . . . ) and a corresponding crest displacement. For example, as seen in FIG. 12, the shaft 22 includes a first offset portion 30A (defining a first lower curve) having a first crest 32A (apex of the curve), a second offset portion 30B (defining a second upper curve) having a crest 32B (apex of the curve), and a third offset 30C having a crest 32C (the tip 28 of the file). In the first offset portion 30A, the shaft 22 extends away from the file axis 26 (e.g., increasing displacement distance) at a shaft location 34A (e.g., near the proximal end 24 of the file 20) and continues to be displaced away from the file axis 26 until its outermost point at the first crest 32A of the first offset portion 30A. From the first crest 32A, the shaft 22 extends towards the file axis 26 such that the amount of displacement decreases (relative to the first crest displacement distance 36A) until the shaft 22 extends to and/or through the file axis 26 at the shaft location 34B (e.g., inflection point). The shaft 22 extends through the file axis 26 at the shaft location 34B to define the second offset portion 30B whereby the shaft 22 once again continues to extend away from the file axis 26 (e.g., increasing displacement distance) to the outermost point of the second offset portion 30B at the second crest 32B. From the second crest 32B, the shaft 22 extends towards the file axis 26 such that the amount of displacement decreases (relative to the second crest displacement distance 36B) until the shaft 22 extends to the file axis 26 at the shaft location 34C. The shaft 22 then extends through the file axis 26 at the shaft location 34C and continues to extend away from the file axis 26 (e.g., increasing displacement distance) to define the third offset portion 30C having a third crest 32C (with a third crest displacement distance 36C) at the tip 28 of the nonlinear file 20.

FIG. 12B shows a nonlinear file 108 having a geometry generally similar to the nonlinear file 20 of FIG. 12A. The nonlinear file 108 may differ from the nonlinear file 20 in that the nonlinear file 108 may include a smaller shaft length and/or overall file length. FIG. 12C shows a nonlinear file 110 having shaft length and/or overall file length generally similar to the nonlinear file 20 of FIG. 12A. The nonlinear file 110 may differ from the nonlinear file 20 in that the nonlinear file 110 may include an additional offset portion offset portion thereby forming multiple bends (e.g., four bends) so that the nonlinear file 110 includes two pairs of upper and lower curves, each curve generally extending to and/or transitioning through the file axis.

Preferably, though not required, crest displacement distance decreases from one offset portion to another offset portion the closer the offset portion may be relative to the tip 28 of the nonlinear file 20. For example, in FIG. 12, the first crest displacement distance 36A may be greater than the second crest displacement distance 36B, which may be greater than the third crest displacement distance 36C. However, it is appreciated than the crest displacement distance may vary from one offset portion to another offset portion or may be the same. Furthermore, it is appreciated that the crest displacement distance may increase or decrease from one offset portion to another offset portion independent of the location of the offset portion relative to the tip 28, the proximal end 24 of the file 20, one or more adjacent offset portions, and/or otherwise.

It is appreciated that the shaft 22 may be displaced from the file axis 26 along the offset portion 30 in an amount greater than about 0.0 mm, preferably greater than about 0.05 mm, and more preferably greater than 0.5 mm. Furthermore, it is appreciated that the shaft 22 may be displaced from the file axis 26 along the offset portion 30 in an amount less than about 7 mm, preferably less than about 6 mm, and more preferably less than about 5 mm. For example, the shaft 22 may be displaced from the file axis 26 along the offset portion 30 in an amount greater than 0.0 mm to about 7 mm, preferably from about 0.05 mm to about 6 mm, and more preferably from about 0.5 mm to about 5 mm.

The present invention may include a fixture 40 for forming the nonlinear file 20. The fixture 40 may be provided in various sizes having any width, length, and/or thickness sufficient for accommodating a dental instrument according to the present invention. In one embodiment, the fixture 40 includes a base 41 having a top surface 42 (e.g., a generally flat surface), a back wall 43, a forward wall 44, and left and right side walls 45. The base includes one or more displacement members 46 that define a nonlinear file path for receiving a conventional dental instrument (e.g., file 10A, 10B, 10C, or otherwise). The base 41 may includes a plurality of displacement members 46 arranged about the base 41 that when contacted by the shaft 22, one or more portions of the shaft 22 may be deflected away from or towards the file axis 26. Optionally, the base 41 may further include one or more guiding members 48 that aid in maintaining portions of the shaft 22 along the file axis 26. It is appreciated that one or more of the displacement members 46, the guiding members or a combination of both may integral with or separate from the base 41. Furthermore, it is appreciated that one or more of the displacement members 46, the guiding members or a combination of both may being fixedly secured to the base or adjustable to alter the nonlinear file path defined thereby. In one specific embodiment as shown in FIG. 13, the base 41 includes a plurality of guiding members 48 having a first pair of corresponding guiding members 50A and 50B and a second pair of guiding members 52A and 52B and a plurality of displacement members 46 having a first displacement member 54, a second displacement member 56, a first pair of corresponding displacement members 58A and 58B, and a second pair of corresponding displacement members 60A and 60B.

The displacement members 46 and guiding members 48 (e.g., pins or otherwise), when included of FIG. 13 extend upward (e.g., generally perpendicularly) from the base 41 and may be situated in a configuration to define a predetermined nonlinear file path. It is appreciated that as a conventional file (e.g., generally linear file) is directed towards one or more of the displacement members 46 and guiding members 48, one or more portions of the shaft 22 may be displaced away from the file axis 26 (e.g., towards the back wall 43 or forward wall 44) or towards the file axis 26 so that the portions of the shaft 22 may conform to the predetermined nonlinear file path of the fixture 40 to orientate the shaft of the conventional file into a nonlinear shape (e.g., a curved file).

More specifically, a conventional file may be inserted into the fixture 40 such that the tip 18 may be first extended through the first pair of corresponding guiding members 50A, 50B and then through the second pair of correspond guiding members 52A,52B. Each guiding member of the corresponding pair may be spaced apart sufficiently to allow the shaft 12 to pass therebetween while generally maintaining the file along the file axis 26. As such, there may be generally little or no shaft displacement from the file axis 26 as the conventional file is guided through each pair of guiding members 46. As the tip 18 of the conventional file continues to be inserted into the fixture, the tip 18 may contact the first displacement member 54A, which preferably deflects the tip 18 away from the file axis 26 (e.g., towards the back wall 43 or the forward wall 44. generally along the top surface 42 and within a common plane). Similarly, as the remaining displacement members 46 are contacted by the tip 18 (as well as various sections of the shaft 12), portions of the conventional file continue to be deflected towards or away from the file axis 26 until the tip 18 reaches (e.g., extends through) the last displacement member 46 (e.g., the pair of corresponding displacement members 60A,60B) such that the shaft 12 of the conventional file may be orientated into the predetermined shape that is defined by the nonlinear file path of the fixture 40. Thereafter, the conventional file being positioned along the nonlinear file path of the fixture 40 may be subjected to a heat-treatment process as discussed below to shape-set the one or more conventional files thereby forming one or more shape-set nonlinear files (e.g., nonlinear file 20 of FIG. 12A, nonlinear file 108 of FIG. 12B, nonlinear file 110 of FIG. 12C, or otherwise).

Various sized conventional files may be accommodated by varying the depth of insertion into the fixture so that the tip 18 extends to (e.g., contacts) the last displacement member 46, the optional guiding member 48, the end of the fixture, or any displacement member/guiding member therebetween until the conventional file is orientated into the predetermined shape. Furthermore, the guiding members, the displacement members, or a combination of both may be secured to the base 41 with sufficient spacing to define the predetermined file path while being able to accommodate various sized files having different thicknesses, tapers, materials and/or lengths.

It is appreciated that in another embodiment, the present invention may accommodate various sized files having different thicknesses, tapers, materials and/or lengths by providing an adjustable fixture 70 having one or more adjustable displacement members 76, one or more adjustable guiding members 78, or a combination of both. The adjustable members 76 and 78 may be configured to allow for repositioning of the at least one member along the top surface 42 of the base 41. More, particularly, the fixture 70 shown in FIG. 14 may include one or more (e.g., two) displacement members (e.g., pins) movable in at least one direction (different direction such as transversely between the back wall 43 and the forward wall 44) to accomplish the desired finished nonlinear geometry of the file.

In doing so, one or more adjustable members may be repositioned generally transversely relative to the file axis 26 (e.g., towards the back wall 43 or the forward wall 44) to accommodate a thicker shaft, a thinner shaft, a shaft having a greater file taper, a shaft having a smaller file taper, or combinations thereof. For example, at least one displacement member and/or guiding members (e.g., 50A, 52A, 58A, 60A) of the corresponding displacement members and/or corresponding guiding members may be transversely repositioned relative to the other corresponding displacement member and/or corresponding guiding member (e.g., 50B, 52B, 58B, 60B), respectively, to increase or decrease the spacing therebetween thereby allowing the fixture to accommodate conventional files having various shaft thicknesses. Furthermore, one or more adjustable members may be repositioned generally transversely relative to the file axis 26 (e.g., towards the back wall 43 or the forward wall 44) to increase or decrease the offset portion 30 transversely thereby increasing or decreasing the crest displacement distance, respectively. For example, by transversely repositioning at least one displacement member 46 (e.g., 54, 56), the shaft 22 may be displaced further away from the file axis 26 thereby forming a greater bend (e.g., curve) with a greater displacement distance.

Optionally or in addition to, one or more adjustable members may be repositioned generally longitudinally relative to the file axis (e.g., towards the left or right side walls 45) to accommodate files of various lengths or to increase or decrease the longitudinal distance of the offset portion 30. It is contemplated that the longitudinal distance of the offset portion 30 may be defined as the distance along the file axis 26 between two adjacent portions of the shaft that intersect the file axis 26 (e.g., the distance along the file axis 26 between shaft locations 34A and 34B, shaft location 34C and the tip 28, or otherwise). For example, the longitudinal spacing between the first pair of corresponding guiding members 50A,50B and the second pair of corresponding displacement members 60A,60B may be increased or decreased generally longitudinally relative left and right side walls 45 to accommodate longer or shorter shafts 22, respectively. Furthermore, the longitudinal distance of the offset portion 30 may be increased or decreased by increasing or decreasing the longitudinal space between two or more of the displacement members 46, the guiding members 48, or combinations of each, respectively. For example, spacing between the second pair of guiding members 52A,52B and the displacement member 56 may be increased or decreased generally longitudinally relative left and right side walls 45 thereby increasing the longitudinal distance therebetween. In this example, increasing or decreasing the longitudinal distance of an offset portion may also include the transverse displacement of the shaft 22 by a displacement member (e.g., displacement member 54), though not required.

Figure 14:
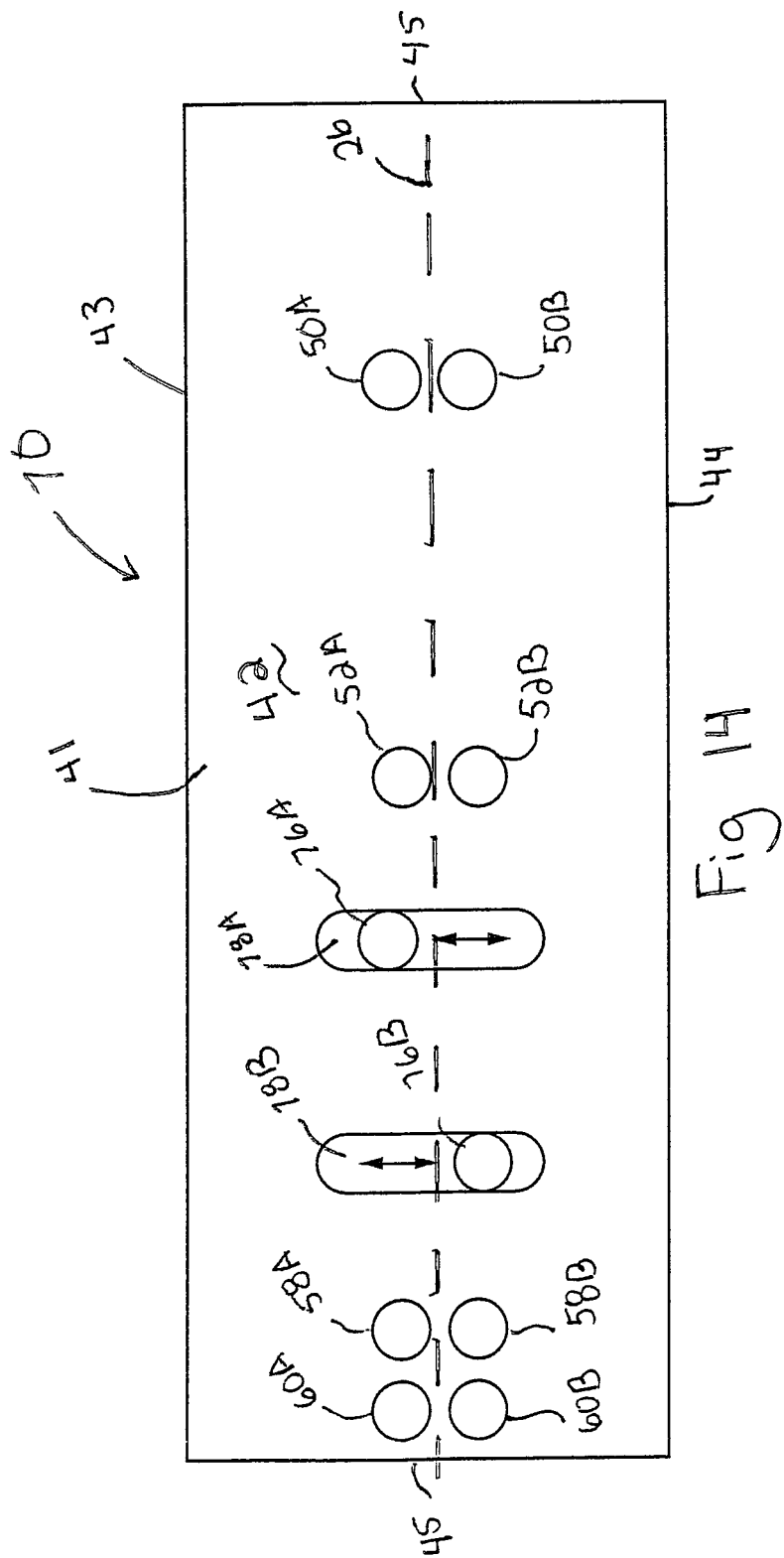
FIG. 14 shows another embodiment of the present invention including a variable fixture for forming the shape-set nonlinear files of FIGS. 12A-12C.
Figure 15A:
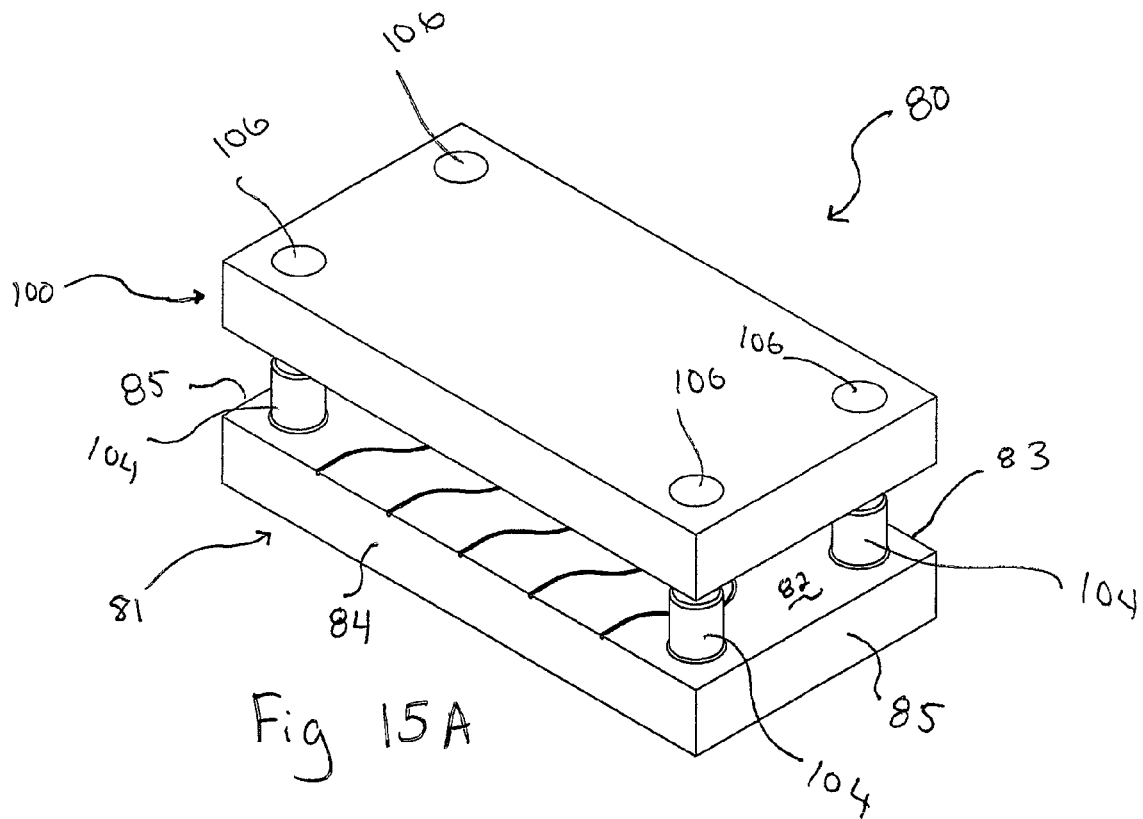
Figure 15B:
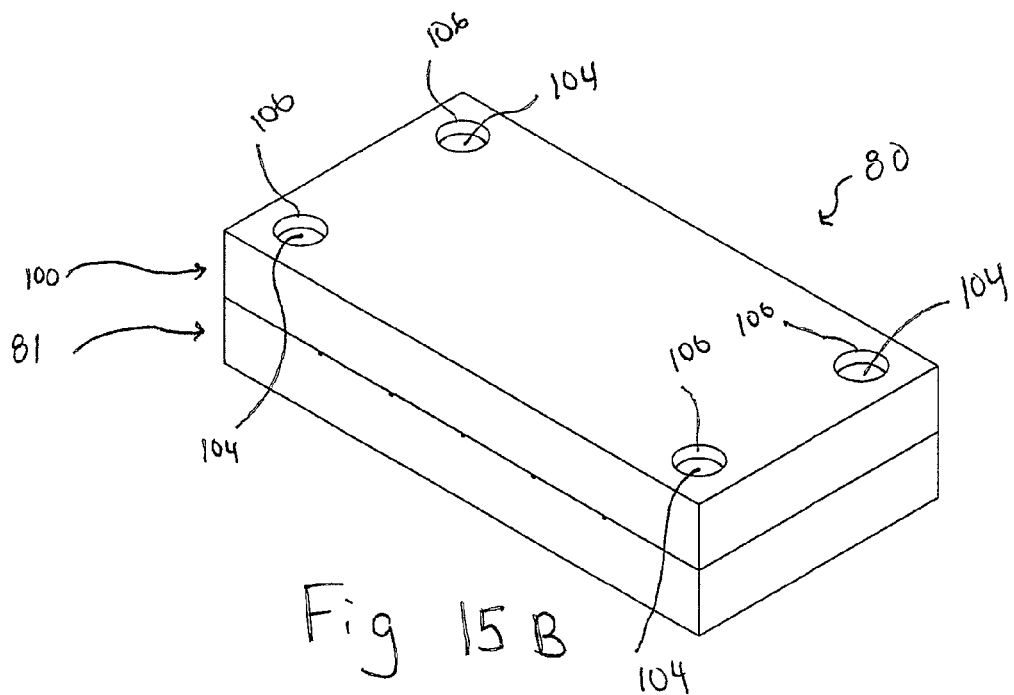

FIG. 14 shows one specific example of an adjustable fixture 50 having similar features as described in the fixture 40 and further including a first adjustable displacement member 76A and a second adjustable displacement member 76B. The adjustable displacement members 76A and 76B may be configured to be adjusted transversely (e.g., towards the back and forward walls 43,44) to increase and/or decrease the offset portions 30A,30B relative to the file axis 26. The adjustable displacement member 76 may be adjusted (or readjusted) prior to, during, and/or after insertion of the conventional file within the fixture 50 to achieve the desired file path for forming the predetermined nonlinear shaped file.

As mentioned above, fixture 50 may include adjustable guiding members (not shown). For purposes of this disclosure, adjustable member may include an adjustable displacement member, an adjustable guiding member, or a combination of both. The adjustable member (e.g., adjustable displacement member 76) may be adjustably secured to the base 41, which allows the adjustable member to be movable within a slot portion 78 (78A,78B) when a different predetermined file path may be desired, to accommodate a different sized conventional file, or otherwise and combinations thereof. It is appreciated that the slot portion 78 may be provided transversely (e.g., generally perpendicularly) relative to the file axis 26 (e.g., extending towards the back or forward walls 43,44 as shown in FIG. 14), longitudinally (e.g., generally parallel) relative to the file axis 26 (e.g., extending towards the left or right side walls 45), diagonally, or otherwise.

Once one or more of the adjustable members have been moved into a desired position to form at least a portion of the predetermined file path, the adjustable member may be temporarily secured into the desired position so as to maintain the portion of the predetermined file path. The adjustable member may then be repositioned to form a different file path if desired. It is appreciated that any adjustable securing means may be utilized sufficient for removeably secure the adjustable member.

In another embodiment of the present invention a fixture may be provided for forming a one or more nonlinear shaped files. As shown in one specific example, 15A-16C provide a fixture 80 that may include a base member 81 having a top surface 82, a back wall 83, a forward wall 84, and left and right side walls 85. The top surface 82 may include at least one groove 90 defining a predetermined file path for receiving a conventional file (e.g., generally linear file). Preferably, the fixture 80 may include a plurality of file grooves 90, which may be similar or vary from one file groove 90 to another. As shown in FIGS. 15A-16C, the fixture 80 includes a plurality of similar grooves 90. The file groove 90 may be formed in a recessed valley of the top surface 82. The file groove 90 may extend (e.g., generally transversely) to one or both of the back wall 83 and the forward wall 84 so that an opening in the respective top and/or bottom walls may extend therethrough as shown in FIG. 16B. Having the file groove extend through at least one of the back and forward walls 83,84 may be desirable to accommodate a handle portion 16, an attachment end 17, the tip end 18, or otherwise, which may be positioned outside or partially outside of the fixture 80. It is further appreciated that the file groove 90 may extend completely within the front surface 82 such that either end of the file groove 90 do not extend through either the back and forward walls 83,84. In this case, the groove 90 may further include a portion sufficiently spaced to accommodate the handle portion 16, the attachment end 17, or otherwise.

Furthermore, the file grove 90 may be of any size or length sufficient to accommodate various sized files. The width and/or height of the file groove 90 may generally correspond to at least the widest and/or thickest portion of the file shaft (e.g., generally near the proximal end of the file) so that file movement (e.g., transverse and/or rotational) may be limited or substantially eliminated. It is possible that the height of the file groove 90 may be less than the height (e.g., thickness) of the file when the cover member 100 further includes a corresponding space (e.g., file groove) to accommodate one or more portions of the file that may extend above the top surface 82.

Preferably, the top surface 82 of the fixture 81 and/or the base of the file groove 90 may be generally flat, though not required. It is appreciated that the top surface 82, the base of the groove 90, or a combination of both may vary (e.g., sloping, curving, and/or otherwise) to accommodate one or more files having the same or different degrees of file taper. As such, the height of the file groove may remain constant or vary depending on whether the top surface 82 and/or the base of the file groove 90 remains generally flat or varies to accommodate various file dimensions (e.g., file taper, height, thickness, and/or otherwise of the file). Desirably, the file groove 90 generally complements the file width and/or height so that file movement (e.g., longitudinally, transversely, radially, or otherwise) may be limited or substantially resisted within the one or more portions of the file groove 90 (e.g., once the file is orientated into a desired position and/or shape within the predetermined file path).

Fixture 80 may also include one or more displacement portions 86, one or more guiding portions 88, or a combination of both that define the predetermined file path and the groove 90. As discussed above, the displacement portion 86 may be generally configured for displacing the shaft 22 from or towards the file axis 26 while the guiding portion 88 may be generally configured for maintaining the shaft 22 and/or proximal end 24 generally along the file axis 26.

Preferably, the fixture 80 may include a plurality of grooves 90, each being defined by one or more displacement portions 86 having a first pair of corresponding displacement portions 92A,92B and a second pair of corresponding displacement portions 94A,94B. The fixture 80 may further include one or more guiding portions 88 having a first pair of corresponding guiding portions 96A,96B and a second pair of corresponding guiding portions 98A,98B to further define each groove 90. Together, the displacement portions 86 and the guiding portions 88 may be positioned to define the groove 90 and a determined file path therein for receiving and orientating portions of a conventional file into a predetermined nonlinear shape (e.g., having one or more curves such as generally an S-shape, C-shape, or otherwise).

The fixture 80 may further include a cover member 100 configured for mating with the base member 81. The cover member 100 may include a bottom surface 101, a top surface 102, a back wall 103, a forward wall 104, and left and right side walls 105. Mating of the base member 81 and the cover member 100 may be accomplished by way of an attachment feature. The attachment feature may be any known structure being capable of removably securing the cover member 100 to the base member 81 so as to generally maintain the file within the file groove 90 while limiting or substantially eliminating movement of the file therein. In one nonlimiting example as shown in FIGS. 15A-16C, the fixture 80 further includes an attachment feature 102 having boss portions 104, which may be configured for being received by corresponding aperture portions 106 thereby generally maintaining the base member 81 relative to the cover member 100 in a closed position. More particularly, after one or more conventional files have been orientated within the one or more file grooves 90, the cover member 100 may be placed over the base member 81 such that the apertures 106 of the cover member 100 are generally aligned with the boss portions 104. The cover member 100 may be then lowered onto the base member 81 such that the top surface 82 of the base member 81 may be proximately located to the bottom surface 101 of the cover member 101. It is appreciated that at least a portion of the top surface 82 may contact at least a portion of the bottom surface 101, and preferably a substantial portion of the top surface 82 may contact a substantial portion of the bottom surface 101, although not required. Once the cover member 100 has been attached to the base member 81 by way of the attachment feature, the one or more files located therein (e.g., with the one or more file grooves 90) are generally maintained in place so that movement of the file within the groove 90 may reduced or substantially eliminated. As such, preferably, the boss portion 104 includes a shape and size (e.g., generally cylindrical or otherwise) that may be dimensioned so as to complement the aperture 104 such that once the boss portion 104 is received by the aperture 104 there may be generally little or substantially no movement within the aperture 106. Thereafter, the one or more conventional files being positioned within the one or more file grooves 90 so as to be orientated along the nonlinear file path of the fixture 80 may be subjected to a heat-treatment process as discussed below to shape-set the one or more conventional files thereby forming one or more shape-set nonlinear files (e.g., nonlinear file 20 of FIG. 12A, nonlinear file 108 of FIG. 12B, nonlinear file 110 of FIG. 12C, or otherwise).

Optionally, the fixture 80 may include one or more adjustable members (not shown). When included, the adjustable members may be movable (and temporarily securable) to provide various file groove designs.

Figure 17:
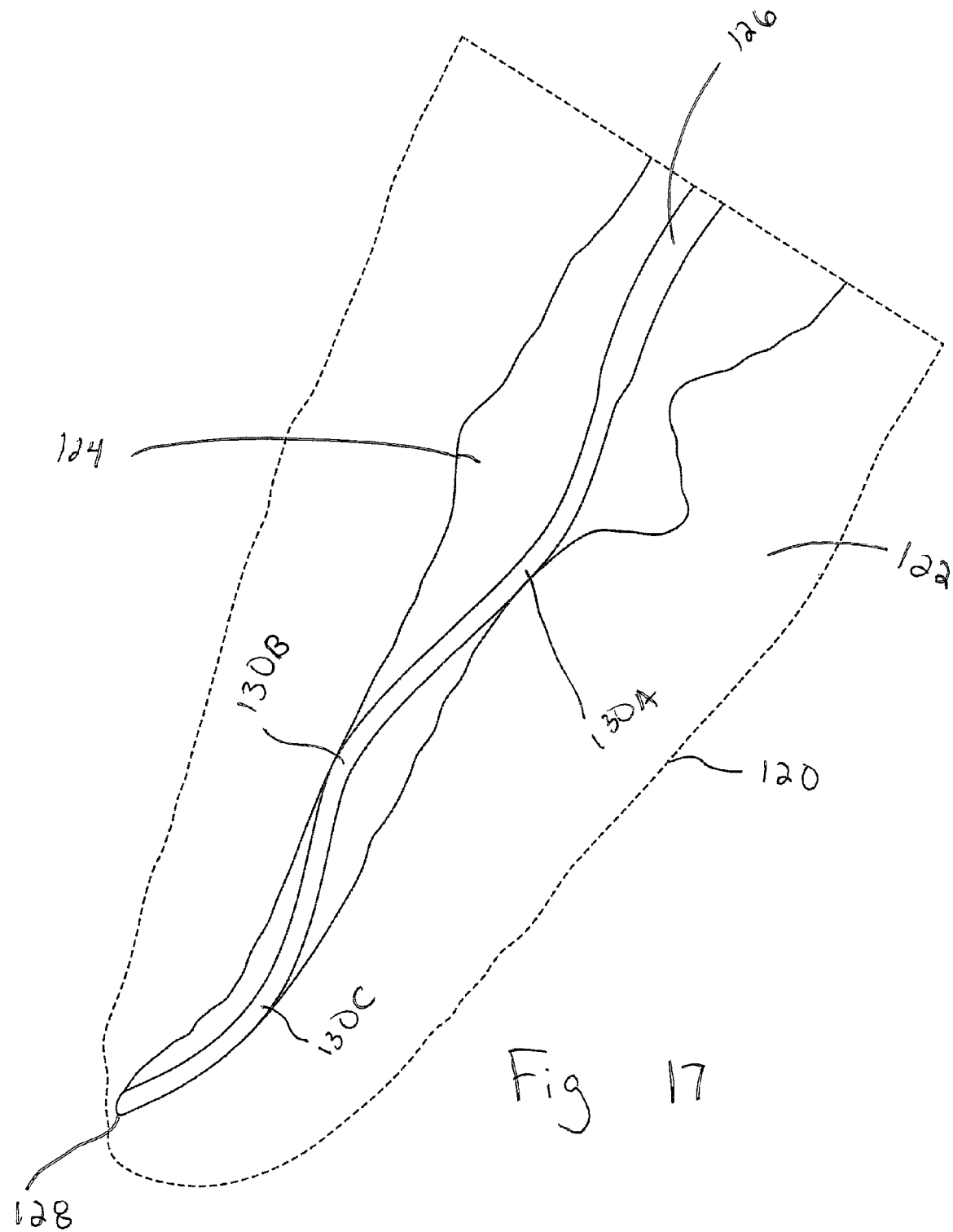
FIG. 17 shows a longitudinal cross-section of a root canal using a shape-set nonlinear file of the present invention during a tooth preparation.

As shown in FIG. 17, a longitudinal cross-sectional view of a tooth portion 120 including dentin 122 generally surrounding a root canal 124 (e.g., pulp and/or nerve tissue) with a root canal wall 125, the root canal 124 being prepared (e.g., cleaned and/or shaped) by one embodiment of the present invention including a shape-set nonlinear file 126. The preparation (e.g., cleaning and/or shaping) of the root canal 124 may include an operator advancing (e.g., urging) (while rotating, reciprocating, oscillating vertically, or otherwise, and combinations thereof) the nonlinear file 126 generally towards the apex 128 of the root canal 124 to remove an infected area that may include pulp along with bacteria, decayed nerve tissue and related debris from the tooth 120. Once the root canal 124 has been cleaned, the root canal 124 may be reshaped and/or enlarged to allow better access for filling thereafter.

It is appreciated that during the removal of the infected area of the root canal 124 and surrounding area, the nonlinear file 126 may typically encounter some resistance as portions of the nonlinear file 126 contacts the material to be removed (e.g., dentin, pulp, nerve tissue and/or infected material) within the tooth. This file resistance and optionally any downward force by the operator towards the apex of the root canal during use of the nonlinear file, may cause the nonlinear file to expand (e.g., generally increase at least one offset portion 130), collapse (e.g., generally decrease at least one offset portion 130), or a combination of both. Expansion and/or collapsing of the offset portion 130 generally may occur in the transverse direction, the longitudinal direction, or a combination of both relative to the file axis so that surface contact with the root canal (e.g., the material to be removed) may be increased. More particularly, as the file resistance occurs (e.g., contacting the dentin and/or root canal wall) one or more offset portion may be deformed along a path of least resistance (e.g., towards the pulp material) so that dentin removal may be minimized while maximizing contact with the pulp material thereby maximizing pulp material removal.

Figure 18:
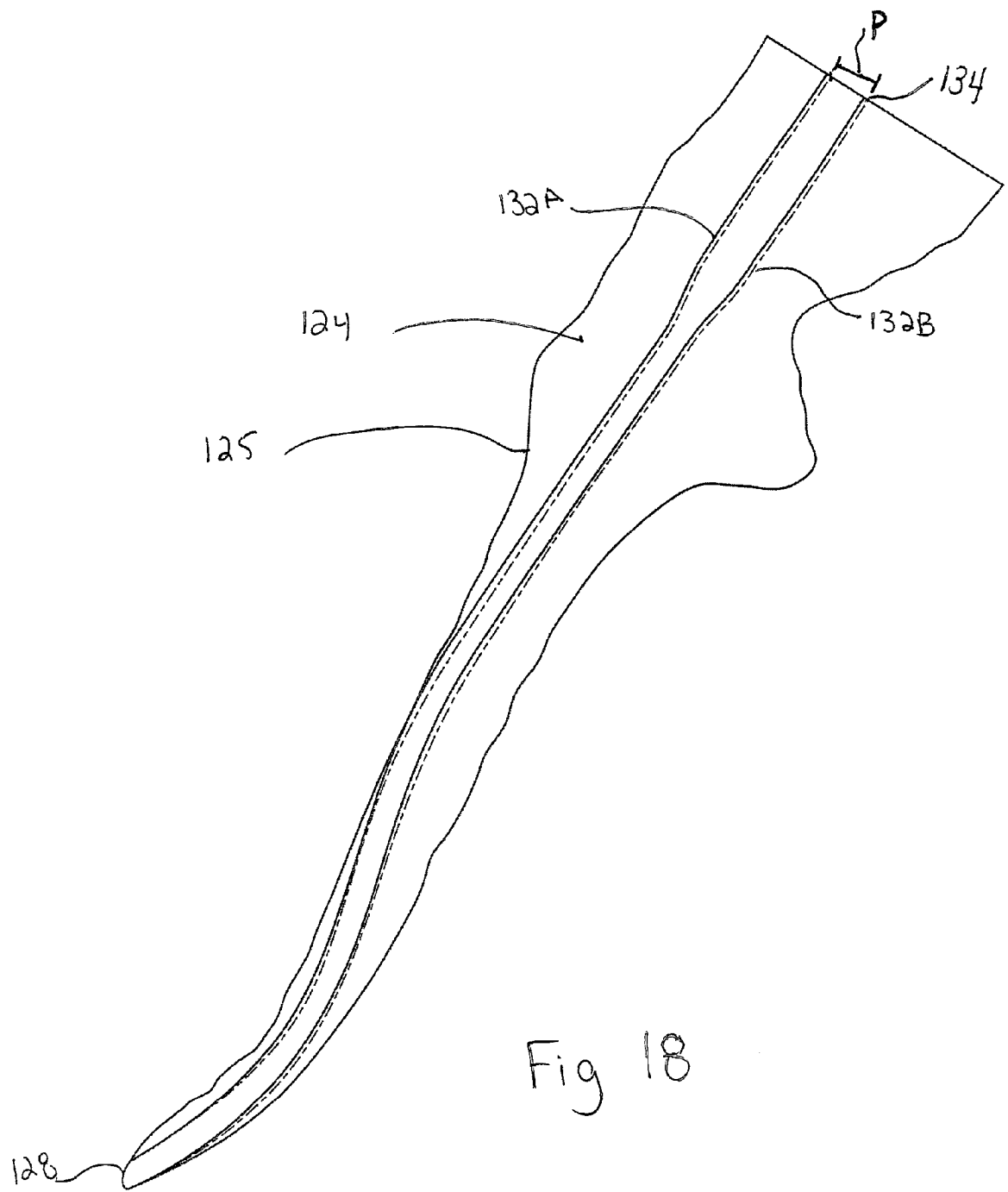
FIG. 18 shows a longitudinal cross-section of a tooth preparation using a conventional linear file during a rotation thereof in the root canal of FIG. 17.

FIG. 18 shows a similar longitudinal cross-sectional view of the root canal 124 shown in FIG. 17 while being cleaned and/or shaped using a comparable conventional linear file 132 (e.g., generally similar shaft length, thickness, and taper). It is believed, that due to the linear shape of the linear file 132, the root canal opening 134 (e.g., file cleaning path) is generally formed having a diameter generally equivalent to the diameter of the shaft of the linear file 132. Linear file 132A and linear file 132B show various positions of the linear file 132 during rotation thereof. As shown in the various positions of the linear file 132A, 132B, there may be generally little or substantially no widening of the root canal opening 134 (e.g., file cleaning path) during the rotation of the conventional linear file 132 (e.g., the root canal opening 134 is generally formed having a diameter substantially similar to the diameter of the shaft of the linear file 132) as shown in FIG. 18.

As such, the nonlinear file 126 of the present invention may provide increased surface contact of the material to be removed within the root canal chamber 124 thereby increasing material removal while cleaning and/or shaping thereof as compared to a comparable conventional linear file having generally the same file width as well as file taper.

Figure 19A:
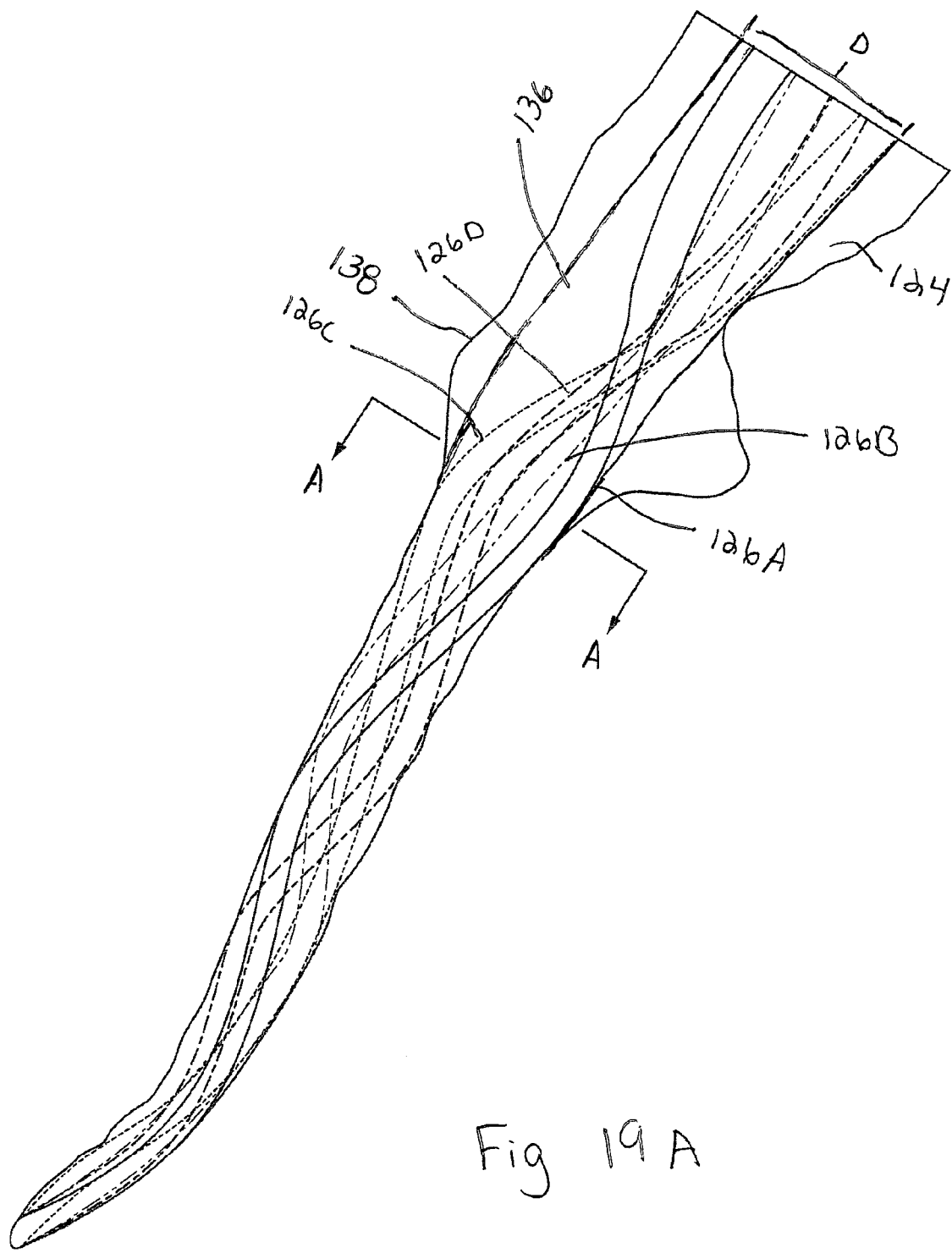
FIG. 19A shows a longitudinal cross-section of a tooth preparation using the shape-set nonlinear file of FIG. 17 during rotation thereof in the root canal of FIG. 17.

FIG. 19A show another longitudinal cross-section of the tooth preparation shown in FIG. 17 including the same nonlinear file 126 through various positions during one rotation of the nonlinear file 126 at generally the same depth within the root canal 124. FIG. 19B shows a transverse cross-section A-A of the tooth preparation shown in FIG. 19A. FIGS. 19A and 19B include a nonlinear file 126A at a first position (e.g., at about 0 degrees of rotation and at about 360 degrees of rotation), a nonlinear file 126B at a second position (e.g., at about 90 degrees of rotation), a nonlinear file 126C at a third position (e.g., at about 180 degrees of rotation), and a nonlinear file 126D at a fourth position (e.g., at about 270 degrees of rotation).

The nonlinear file 126 may be configured to create a root canal opening 136 having a diameter D (e.g., width) greater than the diameter (e.g., width) of the shaft of the nonlinear file 126. It is appreciated that the diameter D may be the same or may be different at different depths along the root canal opening 136. Typically, when referring the diameter D of the root canal opening 136 relative to the diameter of the shaft of the file, both diameters are taken at generally the same relative depth (e.g., transverse cross-section) of the root canal.

The nonlinear file 126 may be configured to create a root canal opening having a diameter at least about 10% greater, at least about 25% greater, at least about 50% greater, and at least about 75% greater than the diameter (e.g., width) of a root canal opening created by the shaft of the nonlinear file 126. Furthermore, the nonlinear file 126 may be configured to create a root canal opening having a diameter less than about 1000% greater, less than about 750% greater, less than about 500% greater, and less than about 200% greater than the diameter of a root canal opening created by the shaft of the nonlinear file 126. For example, the nonlinear file 126 may be configured to create a root canal opening having a diameter ranging from about 10% to about 1000%, from about 25% to about 750%, from about 50% to about 500%, and from about 75% to about 200% greater than the diameter of a root canal opening created by the shaft of the nonlinear file 126. Desirably, the nonlinear file 126 may be configured to create a root canal opening having a diameter ranging from about 100% to about 1000%, and preferably from about 200% to about 500% greater than the diameter of the shaft of the nonlinear file 126. It is appreciated, that the nonlinear file 126 may be configured to create a root canal opening having a diameter (e.g., width) greater than 1000% than the diameter (e.g., width) of a root canal opening created by the shaft of the nonlinear file 126 depending on the downward force of the operator towards the apex of the root canal, the size and/or shape of the root canal, the file stiffness, the size and/or shape of the nonlinear file offset, or otherwise, and combinations thereof. In one specific example, as shown in FIG. 19B, a generally oval shaped root canal opening 136A having an opening wall 137A may be formed from the rotation of the nonlinear file 126. As mentioned above, the shape of the oval shaped root canal opening may be generally influenced by various parameters such as the shape of the root canal 124 (e.g., root canal wall 138) or otherwise. The generally oval shaped root canal opening 132 may include a longitudinal diameter (e.g., generally along the transverse cross-section A-A) and a transverse diameter. More particularly, the longitudinal diameter (e.g., from nonlinear file 126C to nonlinear file 126A) may have a diameter at least about 200% (e.g., at least about 300%) greater than the diameter of the shaft of the nonlinear file 126 and the transverse diameter (e.g., from the nonlinear file 126D to the nonlinear file 26B) may have a diameter at least about 100% (e.g., at least about 200%) greater than the diameter of the shaft of the nonlinear file 126.

The nonlinear file may be configured to form a root canal opening with a diameter being at least about 10% (e.g., 0.1 times), at least about 25%, at least about 50%, and at least about 75% greater than a diameter of a root canal opening formed by a conventional linear file (e.g., having a generally similar shaft length, thickness, and taper of nonlinear file 126). Furthermore, the nonlinear file may be configured to form a root canal opening with a diameter being less than about 1000% (e.g., 10 times), less than about 750%, less than about 500%, and less than about 200% greater than a diameter of a root canal opening formed by a conventional linear file (e.g., having a generally similar shaft length, thickness, and taper of nonlinear file 126). For example, the nonlinear file may be configured to form a root canal opening with a diameter ranging from about 10% to about 1000%, from about 25% to about 750%, from about 50% to about 500%, and from about 75% to about 200% greater than a diameter of a root canal opening formed by a conventional linear file (e.g., having a generally similar shaft length, thickness, and taper of nonlinear file 126). In one specific example for comparing root canal cleaning and/or shaping as shown in the root canals 124 of FIGS. 18 and 19B, it is appreciated that the nonlinear file 126 of the present invention may be configured to provide increased surface contact with the root canal 124 such that a root canal opening 136 may be formed having a diameter D that may be greater than the diameter P of the root canal opening 134 formed by the conventional linear file 132 (e.g., having a generally similar shaft length, thickness, and taper of nonlinear file 126).

In another embodiment, the design and material for the nonlinear file may be configured to adapt to the root canal shape being at least equal to the natural root canal geometry.

In yet another embodiment, the present invention may include a nonlinear file (e.g., dental file) that extends from a file axis in at least two different planes (e.g., three dimensional (3D) space) and methods for forming thereof. FIG. 20 shows a nonlinear file 140 (e.g., cork-screw-like shape, or otherwise) that generally extends along a central file axis 146 and may include an elongated nonlinear shaft portion 142 having a tip 148, a proximal end 144, and a working portion therebetween. The proximal end 144 may be secured to a handle (not shown) or may include an attachment end 147 for attachment to a handpiece (e.g., a rotary device). Similar to the coplanar (e.g., two-dimensional) nonlinear files discussed above, the three-dimensional (e.g., 3D) nonlinear file 140 may be formed in various predetermined nonlinear shapes having different shaft lengths, widths, and/or file taper.

Advantageously, the shaft 142 may include at least one offset portion 150 having at least a portion of the shaft 142 being displaced from the file axis 146 along at least two different planes thereby forming a generally nonlinear (e.g. 3D) file 140. The offset portion 150 may include a crest 152, which generally may be the outermost portion of the shaft 142 along the offset portion 150 relative to the file axis 146. The distance (e.g., transverse distance) from the file axis 146 to the crest 152 (e.g., an internal edge 156 of the crest 152) may be defined by the crest displacement distance 154 (e.g., the maximum displacement distance of the offset portion 150).

It is appreciated that the shaft 142 may extend away from the file axis 146 (and optionally back to the file axis 146) to form a single offset portion 150 having a bend, curve, and/or otherwise. Furthermore, the shaft 142 may extend away from and back to the file axis 146 multiple times to form a plurality of offset portions 150 having a plurality of bends and/or curves similar to the nonlinear files 20,108,110. The offset portion(s) 150 may extend between any portions of the shaft 142, (e.g., generally between the proximal end 144 and the tip end 148). Desirably, the shaft 142 may include a generally continual offset portion 150A as shown in FIG. 20. In this specific embodiment, the continual offset portion 150A of the shaft 142 may extend from a shaft location 156 to the tip 148. As the continual offset portion 150A of the shaft 142 is extended away from the file axis 146 along a displaced file path, a continual displacement distance 158 may be provided defining a distance that the shaft 142 (e.g., internal edge of the shaft 142) is displaced from the file axis 146. The offset portion 150A of the shaft 142 may be continually displaced (e.g., along the displaced file path) from the file axis 146 (e.g. in a generally radially displaced manner) thereby defining a generally spiral-like shape.

It is appreciated that the offset portion 150 of the shaft 142 may be displaced from the file axis 146 (e.g., displacement distance 158) in an amount greater than about 0.0 mm, preferably greater than about 0.05 mm, and more preferably greater than 0.5 mm. Furthermore, it is appreciated that the offset portion 150 of the shaft 142 may be displaced from the file axis 146 in an amount less than about 7 mm, preferably less than about 6 mm, and more preferably less than about 5 mm. For example, the offset portion 150 of the shaft 142 may be displaced from the file axis 146 in an amount greater than 0.0 mm to about 7 mm, preferably from about 0.05 mm to about 6 mm, and more preferably from about 0.5 mm to about 5 mm.

It is further appreciated that at least about 10%, preferably at least about 25%, and more preferably at least about 50% of the shaft 142 (e.g., along one or more longitudinal portions of the shaft between the proximal end and the tip) may be continually displaced radially from the file axis 146. Furthermore, it is appreciated that less than about 100%, preferably less than about 95%, and more preferably less than about 90% of the shaft 142 (e.g., along one or more longitudinal portions of the shaft between the proximal end and the tip) may be continually displaced radially from the file axis 146. For example, from about 10% to about 100%, preferably from about 25% to about 95%, and more preferably from about 5% to about 90% of the shaft 142 (e.g., along one or more longitudinal portions of the shaft between the proximal end and the tip) may be continually displaced radially from the file axis 146.

In this specific example as shown in FIG. 20, the spiral shaped non-linear file 140 includes a continual offset portion 150A. Desirably, the continual offset portion 150A includes an increasing displacement distance 158 as the continual offset portion 150A extends toward the tip 148. When included, the continual offset portion 158A extends from the file axis 146 at a shaft location 194 and continues to be displaced along the remaining portion of the shaft 142 to the tip 148, thereby forming a spaced apart portion 159 therein extending along the file axis 146.

In another embodiment of the present invention having an expandable and/or collapsible design as discussed herein being a generally fluted file formed by wrapping the nonlinear file in to a nonlinear-shape (e.g., by spiraling) resulting in a 3-Dimensional bend instead of a 2-Dimensional bend as shown above.

Figure 22A:
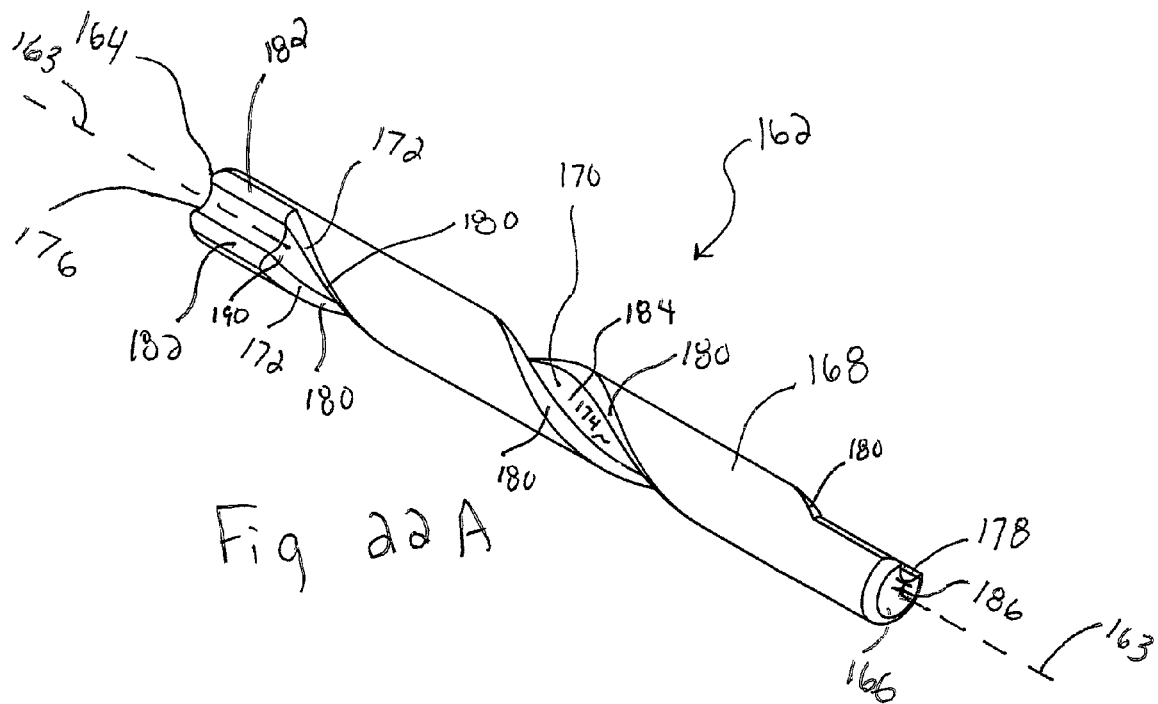
Figure 22B:
Figure 23:
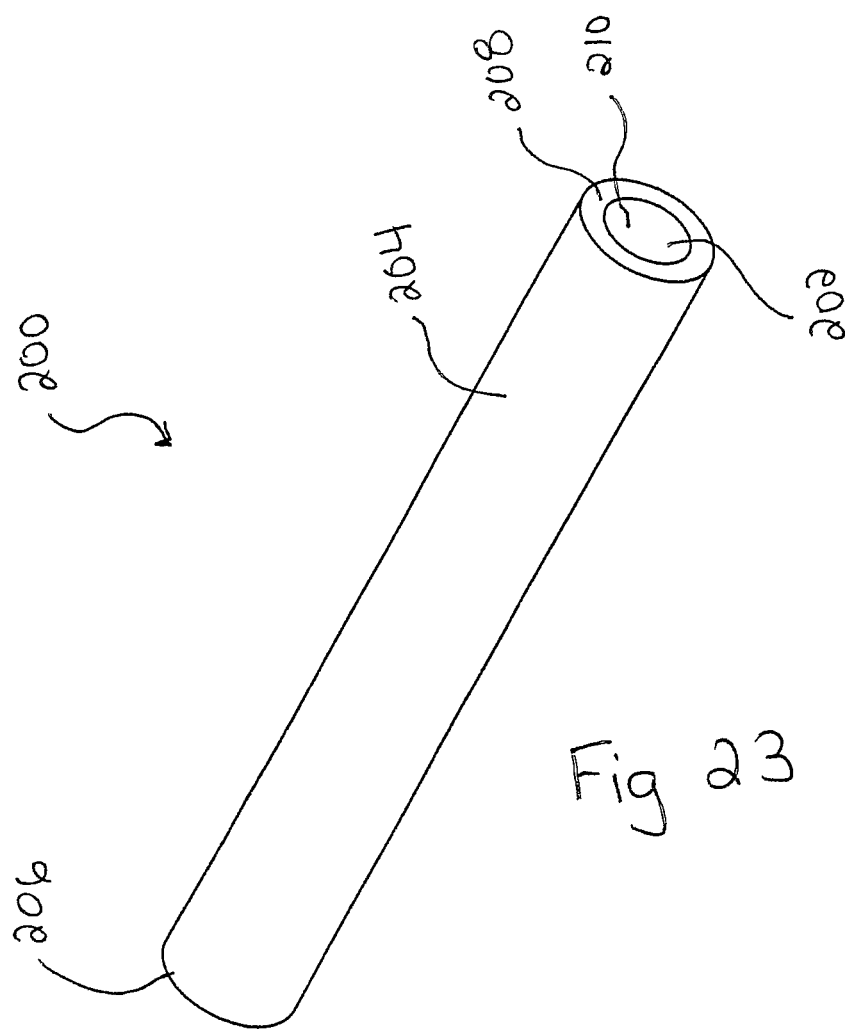

The present invention may include a fixture for forming a nonlinear shaped file extending about at least two planes (e.g., with a three dimensional space). As shown in one specific example, FIGS. 21-23 provide fixture 160 that may include an inner member 162 having a first end 164, a second end 166, an outer surface 168 and a file groove 170 defines a predetermined nonlinear file path for receiving a conventional file (e.g., a generally linear file). The inner member 162 may be a generally cylindrically shaped member, or otherwise shaped member. The inner member 162 generally extends along a fixture axis 163. Desirably, once the shaft 142 is received by the inner member 162, the file axis 163 may extend along the shaft axis 146 or at least may be generally parallel to the shaft axis 146, though not required. Generally, the inner member 162 may be sufficiently sized having a thickness (e.g., width and/or diameter) capable of receiving a file groove 170 formed therein as a recessed valley along the outer surface 168. The recessed valley of the file groove 170 may include side walls 172 and a base surface 174 extending therebetween at a bottom portion of the side walls 172. Desirably, the thickness (e.g., diameter) of the inner member 162 (e.g., generally including the file groove 170) may be greater than the thickness (e.g., width and/or diameter) of the shaft 142 of the nonlinear file 140. The increased thickness of the inner member 162 allows for the formation of the groove 170 being sufficiently sized to receive the shaft 142 while providing one or more displacement portions for displacing one or more portions of the shaft 142 positioned within the groove 170 of the inner member 142.

The file groove 170 may extend (e.g., generally longitudinally) along any portion of the inner member 162, however, preferably the file groove 170 may extend along the outer surface 168 from the first end 164 to the second end 166 of the inner member 162, though not required. More particularly as shown in FIGS. 22A and 22B, the file groove 170 may further include a first opening 176 at the first end 164 for receiving the conventional file and may extend about the inner member 162 therethrough to a second opening 178 at the second end 166. Having the file groove 170 extend through at least one of the first and second ends 164,166 may be desirable to accommodate a handle portion (not shown), an attachment end 147, the tip end 148, or otherwise, which may be positioned outside or partially outside of the fixture 160. It is further appreciated that the file groove 170 may extend completely within the outer surface 168 such that neither end of the file groove 170 extends through the first and second ends 164,166. In this case, the groove 170 may further include a portion sufficiently spaced to accommodate the handle portion, the attachment end, or otherwise.

Furthermore, the file grove 170 may be dimensioned having generally any size or length sufficient to accommodate various sized files. It is appreciated that the width and/or height of the file groove 170 may complement the corresponding portion of the file shaft to be received by the file groove 170. Desirably, the width and/or height of the file groove corresponds to at least the widest and/or thickest portion of the file shaft (e.g., generally near the proximal end of the file) so that file movement may be limited or substantially resisted once the conventional file is positioned within the file groove 170. It is possible that the height of the file groove 170 may be less than the height (e.g., thickness) of the file if a cover member is included having a corresponding space such as a corresponding file groove (not shown) to accommodate one or more portions of the file that may extend above the outer surface 168.

The height of the file groove 170 may be generally constant throughout the length of the file groove 170, though not required. However, it is appreciated that the height of the file groove 170 may vary (e.g., the base 174 and/or the outer surface 168 may slope, curve, bend, and/or otherwise) to accommodate various file dimensions (e.g., file taper, height, thickness, and/or otherwise of the file). Desirably, the file groove 170 generally complements the file dimensions (e.g., width and/or height) so that file movement (e.g., longitudinally, transversely, radially, or otherwise) may be limited or substantially resisted within the one or more portions of the file groove 170 (e.g., once the file is orientated within the predetermined file path of the file groove 170 and into a desired position and/or shape). For example, as shown in FIGS. 22A and 22B, the height of the groove 170 may vary from the first end 164 to the second end 166 with the first end 164 having a greater file groove height (to accommodate the proximal end 144 of the nonlinear file 140 having generally a larger file width) than the second end 166 having a smaller file groove height (to accommodate the tip 148 of the nonlinear file 140 having generally a smaller file width). It is contemplated that the height of the file groove 170 may be generally inversely related to the displacement distance 158 or crest displacement distance. As such, the continual offset set portion 150 of the shaft 142 near the proximal end 144 may have a smaller displacement distance relative to the continual offset portion 150 of the shaft 142 near the tip 148 having a larger displacement distance. Desirably, the height of the file groove 170 generally decreases from the first end 164 to the second end 166 to accommodate the file taper of the conventional file so that the top portion of the file (e.g., the top of the file generally extending between the top portions of the groove side walls 172) may be generally flush with the top surface 168 of the inner member 162, though not required. However, it is appreciated that the height of file may extend above or below the top of the file groove 170.

The inner member 162 may also include one or more displacement portions 180, one or more guiding portions 182, or a combination of both that define the predetermined nonlinear file path and the groove 170. As discussed above, the displacement portion 180 may be generally configured for displacing the shaft 142 away from or towards the file axis 146 while the guiding portion 182 may be generally configured for maintaining the shaft 142 and/or proximal end 144 generally along the file axis 146.

As mentioned above, the file groove 170 may be formed as a recessed valley along the outer surface 168 so that the file groove 170 may extend in a winding-like (e.g., spiral) manner around the cylindrically shaped inner member 162. The groove 170 may be partially wound around the inner member 162 or may be wound around the inner member 162 one or more times. As shown in FIG. 21-22B, the file grove 170 may extend along one complete spiral (e.g., from the first end 164 to a middle portion 184 of the inner member 162) and may continue to extend along a partial spiral (e.g., from the middle portion 184 to the second end 166) around the inner member 162. The inner member 162 may also include fixture displacement distance 186, which may be defined by the distance between the base 174 of the file groove 170 and the fixture axis 163 (and/or the fixture axis 146, when collinear). Similar to the displacement distance 158, the fixture displacement distance 186 defines one or more portions of the shaft 142 that may be displaced from the file axis 146. More particularly, in one specific nonlimiting example as shown in FIGS. 21-22B, the inner member 162 may include a continual (e.g., variable) fixture displacement distance 186 extending generally from a first portion 190 of the inner member 162 proximate to the first end 164 to the second end 166 of the inner member 162. The inner member 162, including the continual fixture displacement distance 186, may result in the nonlinear file 140 having an opening 192 extending longitudinally generally along the file axis 146. It is appreciated that the resultant opening 192 generally extends from a shaft location 194 to the end of the shaft 142 (e.g., tip 148). However, the present invention may not limited to a single and/or continual offset portion 150 and may include a plurality of offset portions 150 such that the shaft 142 may be displaced from and then returned to the file axis 146 one or more times as discussed herein. Desirably, the displacement portions 180, the guiding portions 182 may be positioned to define a the groove 170 and a determined file path therein for receiving and orientating portions of a conventional file into a predetermined nonlinear shape (e.g., having one or more curves such as generally a spiral-shape, corkscrew-shape, or otherwise).

The fixture 160 may further include a cover member 200 configured for mating with the inner member 162. The cover member 200 may include an inner surface 202, an exterior surface 204, each generally extending between a first end 206 and second end 208. Generally, the cover member 200 may be configured to mate with the inner member 162 thereby at least partially enclosing the file groove 170. Desirably, the inner surface 102 of the cover member 200 substantially or completely encloses the file groove 170 while providing an opening and/or throughhole at one or both ends of the file groove 170 (e.g., at the first and/or second ends 164,166 of the inner member 162) to allow the shaft 142 to pass therethrough. More so, it is appreciated that the inner surface 202 be configured to mate with (e.g., correspond or compliment) the exterior surface 168 of the inner member 162. As shown in FIGS. 21 and 23, the cover member 200 may include a generally cylindrical throughhole 210 being defined by the inner surface 202. The cylindrical throughhole 210 may be sufficiently spaced to receive the inner member 162 and the shaft 142 extending therethrough as shown in FIG. 21. Typically, the spacing between the exterior surface 168 of the inner member 162 and the inner surface 204 of the cover member 200 may be minimized to substantially maintain at least a portion of the shaft 142 within the file groove 170 so that the shaft 142 may be generally maintained along the predetermined nonlinear file path. More particularly, the spacing between the exterior surface 168 of the inner member 162 and the inner surface 204 of the cover member 200 may be minimized to reduce or substantially prevent movement (e.g., radially) of the shaft 142 within the file groove 170. The exterior shape of the cover member 200 may be cylindrically shaped as well, however, any shape and/or size of the cover member 200 is contemplated.

Mating of the inner member 162 and the cover member 200 may be accomplished by way by any attachment means known in the art. The attachment means may be by friction fit or by any other attachment means. The attachment means may be any known structure being capable of removably securing the cover member 200 to the inner member 162 so as to generally maintain the shaft 142 within the file groove 170. Optionally, this may be accomplished while also limiting or substantially eliminating movement of the shaft 142 therein. Thereafter, the file (e.g., shaft 142) being positioned within the file groove 170 so as to be orientated along the nonlinear file path of the fixture 160 may be subjected to a heat-treatment process as discussed below to shape-set the conventional file thereby forming a shape-set nonlinear file (e.g., three dimensional spiral-shaped file 140 or otherwise).

In one specific example of forming the nonlinear file 140 as shown in FIG. 21, the method may include wrapping a spiral fluted file (e.g., Nickel Titanium file) around the inner member (e.g., spiral pin). Placing the cover member (e.g., tube cover) over the inner member comprising the fluted file so that the inner member comprising the fluted file may be inserted through the opening of the cover member thereby maintain in the fluted file in spiral-shaped configuration. Optionally, the cover member may be placed over the inner member prior to inserting the fluted file into the fixture (e.g., file groove). Heating the fixture assembly including the fluted file into a heating apparatus (e.g., oven) so that the fluted file may be shape set into the spiral-shaped configuration about the inner member.

As discussed above, the process of producing the shape set dental instrument may include placing a conventional file (e.g., fluted NiTi linear file) into a bending fixture thereby orientating the conventional file into a predetermined shape (e.g., nonlinear shape) and then shape-set heat treating (discussed below) the bending fixture to shape-set the conventional file thereby forming a shape-set nonlinear file corresponding to the predetermined shape. The number of bends (e.g., offset portions) and/or the location of the bends may be chosen from a plurality of configurations in addition to the ones described herein. The fixture design and/or process of shape-setting the file may be produced from various configurations to form a nonlinear file and/or mass production of nonlinear files of the type and design disclosed herein or otherwise. More particularly, the design of the inner member may be varied into a plurality of configurations to form spirals or otherwise having a larger or smaller diameter, degree of overall taper (different from file taper), more or less spirals, or otherwise.

Generally, the method for forming the shape-set nonlinear file may include 1) providing a conventional file (e.g., linear file) having a file axis; 2) provide a fixture having a predetermined nonlinear file path (e.g., 2D, 3D, or otherwise); 3) inserting the conventional file into the fixture so that a first portion of the conventional file (e.g., shaft of the file) may be displaced from the file axis within a first plane (e.g., to form a two dimensional nonlinear file); 4) optionally displacing a second portion of the conventional from the file axis with a second plane being different from the first plane (e.g., to form a three dimensional nonlinear file); and 5) heat-treating the nonlinear file thereby forming a shape-set nonlinear file.

It is appreciated that the heat treatment process for forming a shape-set nonlinear file may include heating a superelastic file to a temperature of at least about 300° C., preferably at least about 350° C., and more preferably at least about 450° C. Furthermore, it is appreciated that the heat treatment process for forming a shape-set nonlinear file may include heating a superelastic file to a temperature less than about 600° C., preferably less than about 550° C. and most preferably less than 500° C. For example, the heat treatment process for forming a shape-set nonlinear file may include heating a superelastic file to a temperature from about 300° C. to about 650° C., preferably from about 350° C. to about 600° C., and more preferably from about 450° C. to about 550° C.

The heat treatment process for forming a shape-set nonlinear file may include heating a superelastic file to a temperature for a time period of at least about 1 minute, preferably at least about 3 minutes, and more preferably at least about 5 minutes to shape-set the superelastic file thereby forming a shape-set nonlinear file. Furthermore, it is appreciated that the heat treatment process for forming a shape-set nonlinear file may include heating a superelastic file to a temperature for a time period of less than about 45 minutes, preferably less than about 30 minutes, and more preferably less than about 20 minutes. For example, the heat treatment process for forming a shape-set nonlinear file may include heating a superelastic file to a temperature for a time period from about 1 minute to about 45 minutes, preferably from about 3 minutes to about 30 minutes, and more preferably from about 5 minutes to about 20 minutes.

The shape-set parameters for the heat treatment process may include heating the material (e.g., Nickel Titanium or otherwise) to a temperature from about 300° C. to about 600° C. (e.g., about 400° C. to about 550° C.) or otherwise for a time period from about 1 minute to about 45 minutes (e.g., about 1 min to about 30 min) or otherwise. In a preferred embodiment of the present invention for shape-setting a file, a typical shape-set temperature and time in the heating apparatus (e.g., oven) may be approximately 500° C. (+/−50° C.) for 10 minutes (+/−5 minutes) which allows the file to take on a different permanent shape (e.g., nonlinear shape).

After the shape-setting heat-treatment, the nonlinear file may be allowed to cool. The cooling step may include gradually reducing the temperature of the heating apparatus, quenching, and/or air cooling the nonlinear file either directly or while within the fixture. Preferably, once the shape-setting heat-treatment has been completed, in the heating apparatus, the fixture may be removed from the heating apparatus and allowed to air cool. Thereafter, once the fixture has been cooled, the file may be removed from the fixture thereby forming a shape-set nonlinear file that may be permanently shape-set into a new nonlinear geometry.

The shape-set endodontic file (e.g., rotary files) contemplated herein, may include one or more bends along the length of the file shaft to ensure maximal surface contact with the root canal as it is being cleaned and shaped during a root canal procedure. It is well known that root canals within a tooth structure are not uniform in cross section. Most root canals are irregular in geometry and can have various cross section geometries including elliptical, ribbon, elongated, narrow, etc. With conventional files (e.g., linear files), the cross-section of the file is generally circular in geometry and therefore typically will remove more of the dentin of the root canal to ensure that all walls of the root canal are cleaned and shaped or less of the dentin of the root canal because either the file is undersized or the root canal geometry is too large to allow for the conventional file to clean it. By having a shape-set nonlinear file, the file may be configured to "expand" thereby maximizing surface contact (e.g., increasing the overall perimeter of the nonlinear file during rotation) will the walls of the root canal that are being cleaned or "collapse" thereby reducing surface contact (e.g., decreasing the overall perimeter of the nonlinear file during rotation) if the root canal walls are narrower than the curves of the shaped file. Overall perimeter of the nonlinear file during rotation, reciprocation, vertical oscillation, or otherwise and combination thereof may be defined as the distance around the perimeter of the opening formed by the nonlinear file during rotation thereof relative to a specific depth of the file within the root canal. It is appreciated that expansion and/or collapsing of the nonlinear file may occur in response to the geometry of the root canal wall 138 (e.g., dentin/pulp interface) changing in the radial direction along various depths (e.g., longitudinal direction) of the root canal. For example, as shown in FIGS. 19A-19B, a root canal opening 136A having an opening wall 137A may be formed during the rotation, reciprocation, vertical oscillation, or otherwise and combination thereof of the nonlinear file 126 at a depth represented by the cross-section A-A. The distance around the opening wall 137A defines the overall perimeter of the root canal opening 136A relative to the depth of the nonlinear file at the cross-section A-A. More particularly, the root canal opening 136 defines the hole/opening created by the nonlinear file during rotation, reciprocation, vertical oscillation, or otherwise and combination thereof and the opening wall 137 defines the material (e.g., dentin, pulp or otherwise material)/hole interface.

Generally, during expansion of the nonlinear file, the amplitude (e.g., displacement distance) of at least one offset portion (e.g., curve portion) may increase (e.g., increasing the displacement distance) thereby generally increasing the overall perimeter formed during rotation of the nonlinear file. It is appreciated that by increasing the overall perimeter during rotation of the nonlinear file, surface contact with the root canal may increase such that a larger root canal opening may be formed. Generally, during the collapse of the nonlinear file, the amplitude of at least one curve portion may decrease (e.g., decreasing the displacement distance), thereby generally decreasing the overall perimeter formed during rotation of the nonlinear file. It is appreciated that by decreasing the overall perimeter formed during rotation of the nonlinear file, surface contact with the root canal may decrease such that a smaller root canal opening may be formed. Desirably, one or more portions of the nonlinear file may expand while one or more other more other portions collapse thereby optimizing surface contact of the nonlinear file with the root canal so that the amount of root canal material removed may be increased relative to a generally similar linear file. Thus, the shape-set nonlinear file may expand and/or collapse where needed within the root canal to optimize root canal cleaning and/or shaping relative to the geometry of the root canal wall.

Factors such as file stiffness may affect the cleaning and/or shaping of a root canal. The amount of stiffness of the shape-set nonlinear file may be optimized to insure that the file may be allowed to expand when the nonlinear file may be shaping and/or cleaning a relatively large portion of the root canal and/or collapse when the nonlinear file may be shaping and/or cleaning a relatively small portion of the root canal by several variables. In one embodiment, the stiffness of the bends (e.g., offset portions) may be controlled by cross-section design of the file. With conventional linear rotary files, the shafts may be available having a file taper where the diameter of the shaft generally increases tip having a certain tip diameter from the file tip (having a certain tip diameter) along the length of the file shaft (or at least a portion thereof). File taper may be generally defined by the rate of increase of the diameter along the length of the file shaft. For example, a file with a 4% taper will generally have about a 0.04 mm diameter increase about every 1.0 mm in length of the shaft portion from the tip of the file. With the shape-set nonlinear files that may configured to expand and/or collapse at one or more offset portions, surface contact with the root canal walls may be generally increased relative to a similar conventional file (e.g., linear file) with a similar taper. Therefore, the ability to increase the overall perimeter of the canal opening formed by the nonlinear file during rotation or otherwise, file taper may be reduced (e.g., reducing shaft stiffness) in the shape-set nonlinear file thereby reducing the cyclic fatigue resistance and flexibility of the nonlinear file. Typically, in order to achieve a similar overall perimeter of a canal opening using a conventional linear file, file taper is greatly increased (e.g., increasing shaft stiffness) thereby increasing cyclic fatigue resistance and flexibility of the nonlinear file. As such, the shape-set nonlinear file may include a lower degree of file taper for forming a canal opening with an overall perimeter relative to a conventional linear file having an increased decree of file taper to form a canal opening having the same overall perimeter.

Stiffness of the nonlinear file may be optimized by increasing mass in cross-section (e.g., greater taper or thicker shaft) to make the nonlinear file stiffer or by decreasing mass in cross-section (e.g., lower taper or thinner shaft) to make the nonlinear file less stiff. By increasing mass in the cross-section may reduce or substantially restrict expansion or collapsing of an offset portion of the file shaft while decreasing mass in the cross-section may increase expansion or collapsing of the offset portion of the file shaft. Optionally or in addition to adjusting the mass of the cross-section, the stiffness of the nonlinear file may be optimized by increasing the number of offset portions (e.g., increasing stiffness) or decreasing the number of offset portions (e.g., decreasing stiffness). Furthermore, stiffness of the nonlinear file may be optimized by increasing the deflection of the offset portions relative to longitudinal axis of the non-linear file (e.g., the distance from the longitudinal axis of the file to the crest of the deflection) to increase stiffness or by decreasing the deflection amount of the offset portions relative to longitudinal file axis of the non-linear file (e.g., the distance from the generally longitudinal file axis of the nonlinear file to the crest and/or inner edge of the offset portion of the shaft) to decrease stiffness.

A secondary heat treatment may be utilized to further control the stiffness of the bends by optimizing the material properties of the file. This may be accomplished by heat treating the shape-set file at certain parameters to adjust the stiffness of the file (e.g., making the file stiffer or less stiff). For example, in one embodiment, a non-superelastic shape set nonlinear file may be formed by further heat treating a shape-set nonlinear file using the heat treatment method described herein for forming a non-superelastic file, though not required. It is appreciated that the heat treatment process for forming a non-superelastic file may generally include heating a superelastic file to a temperature from about 300° C. to about 600° C. (e.g., about 400° C. to about 500° C.) for a period of time from about 20 minutes to about 120 minutes (e.g., about 35 minutes to about 80 minutes, and preferably about 40 minutes to about 70 minutes) thereby increasing the austenite finishing temperature to greater than 20° C. (e.g., greater than about 25° C., and preferably greater than 30° C., between about 20° C. and about 60° C., between about 20° C. and about 40° C., preferably between about 30° C. and about 40° C., and more preferably between 35° C. and about 40° C.) when utilized after the shape-set heat treatment process.

Another method to control the stiffness is by the chemical composition of the Nickel Titanium by adding a Tertiary element to the Nickel Titanium such as Fe, Cu, Cr, etc or by varying the percentages of Nickel, Titanium or the Tertiary element or otherwise as discussed herein.

It is appreciated that the heating step for the non-superelastic heat treatment and/or the nonlinear heat treatment may be accomplished by any known heating means (electrical heating process, radiant or induction heating or may be supplied with a heated fluid such as steam or oil, or otherwise, and any combination thereof) sufficient for heating the instruments to the temperatures described herein. In one preferred embodiment, the heating step may include heating the instrument in a furnace under a controlled atmosphere as discussed herein.

In another embodiment, the heating step may include heating (e.g., selectively heating) an instrument (e.g., one or more portions of the instrument) while optionally inserted into a fixture (for the purpose of altering or maintaining a desired shape profile) as described herein. Temperature control is generally quite important in such processes for the purpose of attaining or maintaining a desired metallurgical state and/or carrying out heat treatment steps such as nitriding and the like. Resistance heating, wherein an electrical current is flowed through the instrument so as to generate heat, may be since resistance heating may be very quick and very controllable so that precise temperatures may be achieved and/or selected regions of the instrument heated.

The heating step when utilizing resistance heating may also include contacting the instrument with a liquid or gaseous fluid during the course of a forming and treatment process. This fluid may comprise a quench fluid used to control the temperature of the instrument, or it may comprise a treatment fluid such as a species which may be chemically reactive with the metal of the instrument; such treatment fluids may comprise nitriding fluids, or otherwise. Otherwise, this fluid may comprise a treatment fluid such as a species which may be chemically unreactive with the metal of the instrument.

Electrical resistance heating may be understood to mean a process wherein a direct or alternating electrical current is applied directly to an instrument so as to cause the heating of that instrument. Generally, an electrical current may be applied directly to the instrument and/or the fixture when included so as to heat that instrument. In one embodiment, the heated instrument or portions of the instrument may be subjected to the heat to maintain the configuration of the instrument while positioned within the fixture in a nonlinear orientation as described herein (e.g., shape-set heat treatment). In other instances, the heating alters a metallurgical state of the instrument. More particularly, electrical resistance heating may enable selective heating for one or more portions of the instrument or may provide heating of the entire instrument to alter the metallurgical state of the instrument or portions thereof as discussed herein (e.g., non-superelastic heat treatment). It is appreciated that one or more portions of the instrument may be selectively heated so that one or more portions of the instrument includes an increased $A_f$ to form a non-superelastic portion while one or more different portions of the instrument may include a different Af (e.g., non-superelastic or superelastic portion). Furthermore, it is appreciated that one or more portions of the instrument may be selectively heated so that the one or more portions of the instrument include an increased $A_f$ to form a non-superelastic portion while one or more different portions of the instrument may include a lower $A_f$ to form a superelastic portion. The degree of heating may be controlled with great precision by controlling the flow of electrical current. Subsequent thereto, the electrical current is terminated, and the instrument is allowed to cool. The profile of the cooling may be controlled by use of quenchants.

It is appreciated that in heating the instrument using resistance heating, a pair of spaced apart electrode contacts, which form an electrically conducting junction to the instrument or a portion therebetween, are in electrical communication with a source of electrical power (e.g., a generator, batteries, or otherwise). Once the contacts are positioned about the instrument, electricity will flow between the spaced apart contacts, thereby providing the heat sufficient for carrying out the specific heat treatment. As discussed above, in some instances, if only certain portions of the instrument are to be subjected to a heat treatment cycle, the contacts may be disposed so as to deliver electrical current only to those portions of the instrument. Accordingly, all of such embodiments are within the scope of this invention. Also, in some instances, certain portions of an instrument may be subjected to specific heat treatment steps separate from the heat treatment steps applied to the remainder of the instrument. For example, an entire instrument may be heat treated so as to induce a first metallurgical transition therein (e.g., non-superelastic heat-treatment), and selected portions of that instrument then retreated to convert those selected portions to a specific geometry (e.g., nonlinear file heat-treatment) and/or a second metallurgical state. For example, an instrument may be so processed to produce a high hardness member having selected areas of low hardness therein.

It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. The present invention also encompasses intermediate and end products resulting from the practice of the methods herein. The use of "comprising" or "including" also contemplates embodiments that "consist essentially of" or "consist of" the recited feature.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method for manufacturing a nonlinear non-superelastic file formed of a material that includes nickel and titanium, the method comprising the steps of:
    providing a superelastic file having a shaft and a file axis;
    providing a fixture including a file groove being defined by one or more displacement members, the file groove configured for receiving the shaft;
    inserting at least a portion of the shaft into the fixture along the file groove, the portion of the shaft including a first portion of the shaft;
    contacting the first portion of the shaft with a first displacement member of the one or more displacement members such that the first portion of the shaft is displaced from the file axis thereby forming a first offset portion of the shaft; and
    heating the portion of the shaft while inserted in the fixture to a temperature from about 450° C. to about 550° C. for a time period from about 5 minutes to about 20 minutes to shape-set the portion of the shaft thereby forming a shape-set nonlinear file;
    cooling the portion of the shaft to form the shape-set nonlinear file and heating at least a portion of the cooled shape-set nonlinear file to a temperature from about 300° C. to about 600° C. for a period of time from about 20 minutes to about 120 minutes to alter the austenite finish temperature thereby forming a shape-set non-superelastic nonlinear file, and wherein the altered austenite finish temperature of the shape-set non-superelastic nonlinear file is from about 20° C. to about 40° C.

2. The method of claim 1, further comprising the step of cooling the portion of the shaft to form the shape-set nonlinear file and heating at least a portion of the cooled shape-set nonlinear file to a temperature from about 400° C. to about 500° C. for a period of time from about 40 minutes to about 70 minutes to alter the austenite finish temperature thereby forming a shape-set non-superelastic nonlinear file, and wherein the altered austenite finish temperature of the shape-set non-superelastic nonlinear file is from about 20° C. to about 40° C.

3. The method of claim 1, wherein the non-superelastic file is formed of a material that includes a shape memory alloy.

4. The method of claim 3, wherein the shape memory alloy is a nickel-titanium based binary alloy.

5. The method of claim 3, wherein the shape memory alloy is a nickel-titanium based ternary alloy.

6. The method of claim 5, wherein the nickel-titanium based ternary alloy of the formula Ni—Ti—X wherein X is Co, Cr, Fe, or Nb.

7. A method for manufacturing a nonlinear superelastic file formed of a material that includes nickel and titanium, the method comprising the steps of:
    providing a superelastic file having a shaft and a file axis;
    providing a fixture including a file groove being defined by one or more displacement members, the file groove configured for receiving the shaft;
    inserting at least a portion of the shaft into the fixture along the file groove, the portion of the shaft including a first portion of the shaft;
    contacting the first portion of the shaft with a first displacement member of the one or more displacement members such that the first portion of the shaft is displaced from the file axis thereby forming a first offset portion of the shaft;
    contacting a second portion of the shaft with a second displacement member of the one or more displacement members such that the second portion of the shaft is displaced from the file axis thereby forming a second offset portion of the shaft, wherein the first offset portion of the shaft and the file axis define a first plane and the second offset portion defines a second plane different from the first plane; and
    heating the portion of the shaft while inserted in the fixture to a temperature of at least about 300° C. for a time period of at least about 1 minute to shape-set the portion of the shaft thereby forming a shape-set nonlinear file.

8. The method of claim 7, wherein during the heating step, the portion of the shaft is heated to a temperature from about 300° C. to about 650° C. for a time period from about 1 minute to about 45 minute to shape-set the portion of the shaft thereby forming the shape-set nonlinear file.

9. The method of claim 7, wherein during the heating step, the portion of the shaft is heated to a temperature from about 350° C. to about 600° C. for a time period from about 3 minutes to about 30 minutes to shape-set the portion of the shaft thereby forming the shape-set nonlinear file.

10. The method of claim 7, wherein during the heating step, the portion of the shaft is heated to a temperature from about 450° C. to about 550° C. for a time period from about 5 minutes to about 20 minutes to shape-set the portion of the shaft thereby forming the shape-set nonlinear file.

11. The method of claim 10, further comprising the step of cooling the portion of the shaft to form the shape-set nonlinear file and heating at least a portion of the cooled shape-set nonlinear file to a temperature from about 300° C. to about 600° C. for a period of time from about 30 minutes to about 120 minutes to alter the austenite finish temperature thereby forming a shape-set non-superelastic nonlinear file, and wherein the altered austenite finish temperature of the shape-set non-superelastic nonlinear file is from about 20° C. to about 40° C.

12. The method of claim 10, further comprising the step of cooling the portion of the shaft to form the shape-set nonlinear file and heating at least a portion of the cooled shape-set nonlinear file to a temperature from about 400° C. to about 500° C. for a period of time from about 40 minutes to about 70 minutes to alter the austenite finish temperature thereby forming a shape-set non-superelastic nonlinear file, and wherein the altered austenite finish temperature of the shape-set non-superelastic nonlinear file is from about 20° C. to about 40° C.

13. The method of claim 7, wherein the superelastic file is formed of a material that includes a shape memory alloy.

14. The method of claim 13, wherein the shape memory alloy is a nickel-titanium based binary alloy.

15. The method of claim 13, wherein the shape memory alloy is a nickel-titanium based ternary alloy.

16. The method of claim 15, wherein the nickel-titanium based ternary alloy of the formula Ni—Ti—X wherein X is Co, Cr, Fe, or Nb.

17. A method for manufacturing a nonlinear superelastic file formed of a material that includes nickel and titanium, the method comprising the steps of:
  providing a superelastic file having a shaft and a file axis;
  providing a fixture including a file groove being defined by one or more displacement members, the file groove configured for receiving the shaft;
  inserting at least a portion of the shaft into the fixture along the file groove, the portion of the shaft including a first portion of the shaft;
  contacting the first portion of the shaft with a first displacement member of the one or more displacement members such that the first portion of the shaft is displaced from the file axis thereby forming a first offset portion of the shaft; and
  heating the portion of the shaft while inserted in the fixture to a temperature of at least about 300° C. for a time period of at least about 1 minute to shape-set the portion of the shaft thereby forming a shape-set nonlinear file;
  wherein the one or more displacement members further includes a second displacement member and the file groove is further defined by a pair of guiding members for receiving a guide portion of the shaft therebetween, the pair of guiding members being configured for maintaining the guide portion of the shaft from being displaced from the file axis while the first displacement member displaces the first portion of the shaft away from the file axis and the second displacement member displaces a portion of the shaft towards the file axis.

18. The method of claim 17, wherein during the heating step, the portion of the shaft is heated to a temperature from about 300° C. to about 650° C. for a time period from about 1 minute to about 45 minute to shape-set the portion of the shaft thereby forming the shape-set nonlinear file.

19. The method of claim 17, wherein during the heating step, the portion of the shaft is heated to a temperature from about 350° C. to about 600° C. for a time period from about 3 minutes to about 30 minutes to shape-set the portion of the shaft thereby forming the shape-set nonlinear file.

20. The method of claim 17, wherein the first displacement member, the second displacement member, and the pair of guiding members defining the file groove form a predetermined curved nonlinear file path that orientates the portion of the shaft into a generally C-shaped profile.

21. The method of claim 17, wherein the superelastic file is formed of a material that includes a shape memory alloy.

22. The method of claim 21, wherein the shape memory alloy is a nickel-titanium based binary alloy.

23. The method of claim 21, wherein the shape memory alloy is a nickel-titanium based ternary alloy.

24. The method of claim 23, wherein the nickel-titanium based ternary alloy of the formula Ni—Ti—X wherein X is Co, Cr, Fe, or Nb.

25. A method for manufacturing a nonlinear superelastic file formed of a material that includes nickel and titanium, the method comprising the steps of:
  providing a superelastic file having a shaft and a file axis;
  providing a fixture including a file groove being defined by one or more displacement members, the file groove configured for receiving the shaft;
  inserting at least a portion of the shaft into the fixture along the file groove, the portion of the shaft including a first portion of the shaft;
  contacting the first portion of the shaft with a first displacement member of the one or more displacement members such that the first portion of the shaft is displaced from the file axis thereby forming a first offset portion of the shaft; and
  heating the portion of the shaft while inserted in the fixture to a temperature of at least about 300° C. for a time period of at least about 1 minute to shape-set the portion of the shaft thereby forming a shape-set nonlinear file;
  wherein the one or more displacement members further includes a second displacement member and a third displacement member, and the file groove is further defined by a pair of guiding members for receiving a guide portion of the shaft therebetween, the pair of guiding members being configured for maintaining the guide portion of the shaft from being displaced from the file axis while the first displacement member displaces the first portion of the shaft away from the file axis, the second displacement member displaces a second portion of the shaft away from the first displacement member and back through the file axis, and the third displacement member displaces the a third portion of the shaft from the second displacement member and towards the file axis.

26. The method of claim 25, wherein the first displacement member, the second displacement member, the third displacement member, and the pair of guiding members that define the file groove form a predetermined curved nonlinear file path having at least two arcuate portions that orientate the portion of the shaft into a generally S-shaped profile.

27. The method of claim 25, wherein during the heating step, the portion of the shaft is heated to a temperature from about 300° C. to about 650° C. for a time period from about 1 minute to about 45 minute to shape-set the portion of the shaft thereby forming the shape-set nonlinear file.

28. The method of claim 25, wherein during the heating step, the portion of the shaft is heated to a temperature from about 350° C. to about 600° C. for a time period from about 3 minutes to about 30 minutes to shape-set the portion of the shaft thereby forming the shape-set nonlinear file.

29. The method of claim 25, wherein the superelastic file is formed of a material that includes a shape memory alloy.

30. The method of claim 29, wherein the shape memory alloy is a nickel-titanium based binary alloy.

31. The method of claim 29, wherein the shape memory alloy is a nickel-titanium based ternary alloy.

32. The method of claim 31, wherein the nickel-titanium based ternary alloy of the formula Ni—Ti—X wherein X is Co, Cr, Fe, or Nb.

33. A method for manufacturing a nonlinear superelastic file formed of a material that includes nickel and titanium, the method comprising the steps of:
providing a superelastic linear file having a shaft and a file axis;
providing a fixture including an inner member and an cover member, at least one of the inner member and the cover member having a file groove being defined by one or more displacement members, the file groove being configured for receiving the shaft and at least a portion of the file groove extending along a predetermined nonlinear file path in a spiral-like manner;
inserting at least a portion of the shaft into the fixture along the file groove, the portion of the shaft including a first portion of the shaft;
contacting the first portion of the shaft with a first displacement member of the one or more displacement members such that the first portion of the shaft is displaced from the file axis thereby forming a first offset portion of the shaft, the first offset portion of the shaft and the file axis defining a first plane;
contacting a second portion of the portion of the shaft with a second displacement member of the one or more displacement members such that the second portion of the shaft is displaced from the file axis thereby forming a second offset portion of the shaft, the second offset portion of the shaft defines a second plane different from the first plane; and
heating the portion of the shaft to a temperature of at least about 300° C. for a time period of at least about 5 minutes to shape-set the portion of the shaft thereby forming a shape-set nonlinear file.

34. The method of claim 33, wherein during the heating step, the portion of the shaft is heated to a temperature from about 300° C. to about 650° C. for a time period from about 5 minutes to about 45 minutes to shape-set the portion of the shaft thereby forming the shape-set nonlinear file.

35. The method of claim 33, wherein during the heating step, the portion of the shaft is heated to a temperature from about 350° C. to about 600° C. for a time period from about 3 minutes to about 30 minutes to shape-set the portion of the shaft thereby forming the shape-set nonlinear file.

36. The method of claim 35, wherein the file groove extends along the inner member, the cover member, or a portion of both the inner member and the cover member in the spiral-like manner.

37. The method of claim 35, wherein the cover member at least partially covers the portion of the file groove extending in a spiral-like manner so that upon inserting the portion of the shaft into the fixture, the portion of the shaft is maintained within the file groove.

38. The method of claim 35, wherein the inner member includes a fixture axis that is generally co-linear with the file axis such that the portion of the file groove extending in a spiral-like manner is continually displaced from the fixture axis thereby continually displacing a corresponding portion of the shaft extending therein from the file axis.

39. The method of claim 35, wherein the shaft includes a shaft length and at least about 50% of the shaft length is continually displaced radially from the file axis.

40. The method of claim 33, wherein during the heating step, the portion of the shaft is heated to a temperature from about 450° C. to about 550° C. for a time period from about 5 minutes to about 20 minutes to shape-set the portion of the shaft thereby forming the shape-set nonlinear file.

41. The method of claim 40, further comprising the step of cooling the portion of the shaft to form the shape-set nonlinear file and heating at least a portion of the cooled shape-set nonlinear file to a temperature from about 300° C. to about 600° C. for a period of time from about 30 minutes to about 120 minutes to alter the austenite finish temperature thereby forming a shape-set non-superelastic nonlinear file, and wherein the altered austenite finish temperature of the shape-set non-superelastic nonlinear file is from about 20° C. to about 40° C.

42. The method of claim 40, further comprising the step of cooling the portion of the shaft to form the shape-set nonlinear file and heating at least a portion of the cooled shape-set nonlinear file to a temperature from about 400° C. to about 500° C. for a period of time from about 40 minutes to about 70 minutes to alter the austenite finish temperature thereby forming a shape-set non-superelastic nonlinear file, and wherein the altered austenite finish temperature of the shape-set non-superelastic nonlinear file is from about 20° C. to about 40° C.

43. The method of claim 33, wherein the nonlinear file is formed of a material that includes a shape memory alloy.

44. The method of claim 43, wherein the shape memory alloy is a nickel-titanium based binary alloy.

45. The method of claim 43, wherein the shape memory alloy is a nickel-titanium based ternary alloy.

46. The method of claim 45, wherein the nickel-titanium based ternary alloy of the formula Ni—Ti—X wherein X is Co, Cr, Fe, or Nb.

* * * * *